United States Patent
Ahmed et al.

(10) Patent No.: US 9,522,907 B2
(45) Date of Patent: Dec. 20, 2016

(54) ANTICANCER AGENT AND PROCESS FOR THE PREPARATION THEREOF

(71) Applicant: COUNCIL OF SCIENTIFIC & INDUSTRIAL RESEARCH, New Delhi (IN)

(72) Inventors: Kamal Ahmed, Hyderabad (IN); Srinivasa Reddy Telukutla, Hyderabad (IN); Srinivasulu Vunnam, Hyderabad (IN); Venkata Subbarao Ayinampudi, Hyderabad (IN); Shankaraiah Nagula, Hyderabad (IN); Venkata Phani Surya Vishnu Vardhan Madugulla, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/793,553

(22) Filed: Jul. 7, 2015

(65) Prior Publication Data
US 2016/0002214 A1    Jan. 7, 2016

(30) Foreign Application Priority Data
Jul. 7, 2014    (IN) .......................... 1846/DEL/2014

(51) Int. Cl.
| | |
|---|---|
| *A01N 43/82* | (2006.01) |
| *A61K 31/41* | (2006.01) |
| *C07D 413/10* | (2006.01) |

(52) U.S. Cl.
CPC .................. *C07D 413/10* (2013.01)

(58) Field of Classification Search
None
See application file for complete search history.

(56) References Cited

U.S. PATENT DOCUMENTS 6,589,971 B1 * 7/2003 Neidle ............... A61K 31/4184
514/394

OTHER PUBLICATIONS

Jessen, Katayoun A. et al.: "*The discovery and mechanism of action of novel tumor-selective and apoptosis-inducing 3,5-diaryl-1,2,4-oxadiazole series using a chemical genetics approach*"; Mol Cancer Ther 2005;4(5). May 2005, p. 761-771.
Jordan, Allan et al.: "*Tubulin as a Target for Anticancer Drugs: Agents Which Interact with the Mitotic Spindle*"; Med. Res. Rev., 18, No. 4, 259-296, 1998.
Kumar, Dalip et al.: "*Synthesis of novel 1,2,4-oxadiazoles and analogues as potential anticancer agents*"; European Journal of Medicinal Chemistry 46 (2011) 3085-3092.
Kundu, Mrityunjoy et al.: "*Synthesis and Anticancer Activity of 3, 5-Diaryl 1, 2, 4-Oxadiazole Derivatives*"; Ind J Pharm Edu Res, Jul.-Sep. 2011, vol. 45, Issue 3, p. 267-271.
Singh, Malvinder P. et al.: "*Synthesis and Sequence-Specific DNA Binding of a Topoisomerase Inhibitory Analog of Hoechst 33258 Designed for Altered Base and Sequence Recognition*"; Chem. Res. Toxicol, 1992, 5, 597-607.
Singhal, Nidhi et al.: "*Synthesis of Amidine and Bis Amidine Percursors*"; Sulfur and Silicon, 2001, vol. 174. pp. 141-192.
Vasquez, Robert J. et al.: "*Nanomolar Concentrations of Nocodazole Alter Microtubule Dynamic Instability In Vivo and In Vitro*"; Molecular Biology of the Cell, vol. 8, 973-985, Jun. 1997.
White, Alex W. et al.: "*Resistance-Modifying Agents, 9. Synthesis and Biological Properties of Benzimidazole Inhibitors of the DNA Repair Enzyme Poly(ADP-ribose) Polymerase*"; J. Med. Chem. 2000, 43, 4084-4097.

* cited by examiner

Primary Examiner — Jean Cornet
(74) Attorney, Agent, or Firm — DLA Piper LLP (US)

(57) ABSTRACT

The present invention provides a compound of general formula A for use as a potential anticancer agent against human cancer cell lines and a process for the preparation thereof General formula A

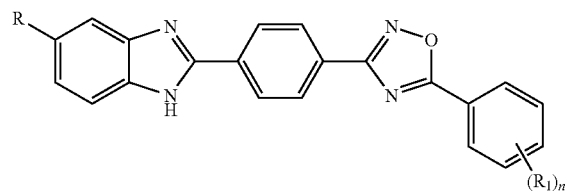

wherein
R is selected from the group consisting of H, F, Cl, Br, OMe, Me and $CF_3$,
$R_1$ is selected from the group consisting of H, 4-F, 4-Cl, 4-Br, 4-$CF_3$, 4-OMe, 3,4-OMe, 3,5-OMe and 3,4,5-OMe, and
n is an integer ranging from 1-3.

6 Claims, No Drawings

ANTICANCER AGENT AND PROCESS FOR THE PREPARATION THEREOF

BACKGROUND OF THE INVENTION

Field of the Invention

The present invention relates to 3-[4-(1H-Benzo[d]imidazol-2-yl)phenyl]-5-phenyl-1,2,4-oxadiazole derivatives of general formula A as anticancer agents. The present invention also relates to a process for the preparation of 3-[4-(1H-Benzo[d]imidazol-2-yl)phenyl]-5-phenyl-1,2,4-oxadiazole derivatives of general formula A.

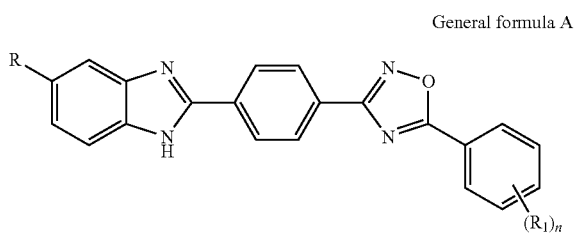

General formula A wherein:
R is selected from the group consisting of H, F, Cl, Br, OMe, Me and $CF_3$,
$R_1$ is selected from the group consisting of H, 4-F, 4-Cl, 4-Br, 4-$CF_3$, 4-OMe, 3,4-OMe, 3,5-OMe and 3,4,5-OMe, and
n is an integer ranging from 1-3.

Background Information

Small molecules have attracted much attention in chemistry, biology and particularly in medicine field for the past few years, which affect tubulin polymerisation. (Jordan, A.; Hadfield, J. A.; Lawrence, N. J.; McGown, A. T. Tubulin as a Target for Anticancer Drugs: Agents which Interact with the Mitotic Spindle. *Med. Res. Rev.* 1998, 18, 259-296). The targeting of tubulin is an important mechanism for cancer chemotherapy and these tubulin binding agents (taxanes and vinca alkaloids) have played a crucial role in the treatment of diverse human cancers. (Jordan, M. A.; Wilson, L. Microtubules as a target for Anticancer Drugs. *Nat. Rev. Cancer* 2004, 4, 253-265). Despite of their wide clinical applications, there are several limitations for these derivatives such as poor water solubility, development of drug resistance, toxic effects which has inspired to further search for new effective antitumor agents that target tubulin. Therefore identification of new molecules with tubulin binding mechanism and with minimal toxicity to the normal tissue is attractive for the discovery and development of novel anticancer agents.

Benzimidazole substituted derivatives are known as inhibitors of tubulin polymerisation and are useful for inhibiting cell proliferation for the treatment of cancer. (Vasquez, R. J.; Howell, B.; Yvon, A. M.; Wadsworth, P. Cassimeris, L. *Mol. Biol. Cell* 1997, 8, 973). Among the anticancer benzimidazoles, an important position is held by 2-aryl/heteroarylbenzimidazole derivatives that are found to be more potent and hence the design and synthesis of 2-aryl benzimidazoles are the potential area of research. (White, A. W.; Almassy, R.; Calvert, A. H.; Curtin, N. J.; Griffin, R. J.; Hostomsky, Z.; Newell, D. R.; Srinivasan, S.; Golden, B. T. *J. Med. Chem.* 2000, 43, 4084). For instance, Bisbenzimidazole derivatives such as Hoechst 33258 has undergone Phase II clinical evaluation as an anticancer agent and the inhibition of topoisomerase and DNA helicase has been proposed as its mechanism of action. (Singh, M. P., Joseph, T., Kumar, S., Bathini, Y., Lown, J. W., *Chem. Res. Toxicol.* 1992, 5, 597-607)

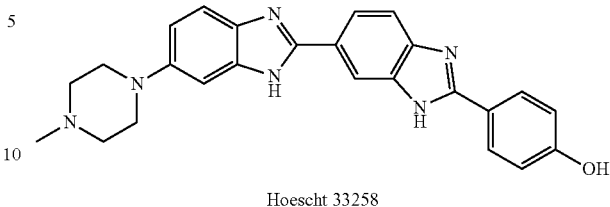

Hoescht 33258

Similarly, there has been wide interest in compounds containing the 1,2,4-oxadiazole scaffold because of their broad range of biological activities such as antimicrobial, antiviral, anti inflammatory, and antineoplastic. (Kumar, D.; Patel, G.; Chavers, A. K.; Chang, K. H.; Shah, K. *Eur. J Med. Chem.* 2011, 46, 3085). Among the oxadiazoles, the 3,5-disubstituted-1,2,4-oxadiazoles derivatives are reported in literature for their anticancer potential. (Jessen, K. A.; English, N. M.; Wang, J. Y.; Maliartchouk, S.; Archer, S. P.; Qiu, L.; Brand, R.; Kuemmerle, J.; Zhang, H. Z.; Gehlsen, K.; Drewe, J.; Tseng, B.; Cai, S. X.; Kasibhatla, S. *Mol. Cancer Ther.* 2005, 4, 761). References may be made of Journal of pharmaceutical Education and Research 2011, 45, 267" by Mrityunjoy Kundu et al, wherein benzimidazole derivatives as 3,5-Diaryl-1,2,4-Oxadiazole as anticancer agents.

The present inventors have found out that by incorporating 2-aryl benzimidazole with oxadiazole scaffold. enhanced anticancer activity can be achieved that might work through inhibition of tubulin polymerization.

OBJECTIVES OF THE INVENTION

The main objective of the present invention is to provide 3-[4-(1H-Benzo[d]imidazol-2-yl)phenyl]-5-phenyl-1,2,4-oxadiazole derivatives of general formula A useful as antitumor agents.

Another object of this invention is to provide a process for the preparation of 3-[4-(1H-Benzo[d]imidazol-2-yl)phenyl]-5-phenyl-1,2,4-oxadiazole derivatives of general formula A.

SUMMARY OF THE INVENTION

Accordingly, present invention provides a compound of general formula A

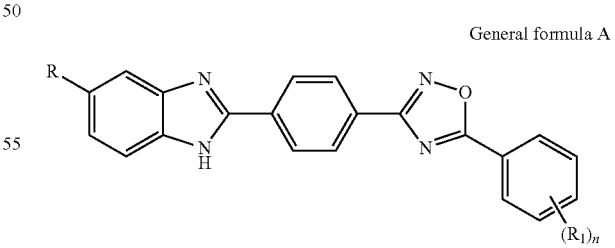

General formula A wherein
R is selected from the group consisting of H, F, Cl, Br, OMe, Me and $CF_3$
$R_1$ is selected from the group consisting of H, 4-F, 4-Cl, 4-Br, 4-$CF_3$, 4-OMe, 3,4-OMe, 3,5-OMe and 3,4,5-OMe; and
n is an integer ranging from 1-3.

In an embodiment of the present invention, the compound of general formula A is selected from the group consisting of:

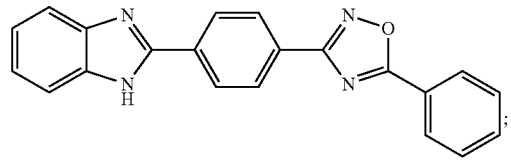

3-(4-(1H-Benzo[d]imidazol-2-yl)phenyl)-5-
phenyl-1,2,4-oxadiazole
(1a)

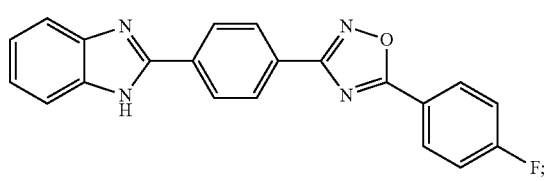

3-(4-(1H-Benzo[d]imidazol-2-yl)phenyl)-5-
(4-fluorophenyl)-1,2,4-oxadiazole
(1b)

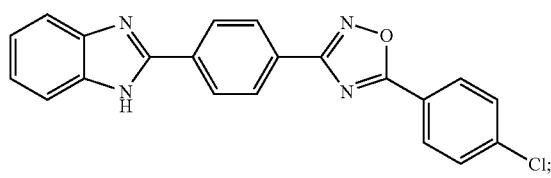

3-(4-(1H-Benzo[d]imidazol-2-yl)phenyl)-5-
(4-chlorophenyl)-1,2,4-oxadiazole
(1c)

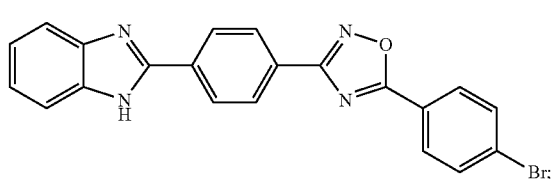

3-(4-(1H-Benzo[d]imidazol-2-yl)phenyl)-5-
(4-bromophenyl)-1,2,4-oxadiazole
(1d)

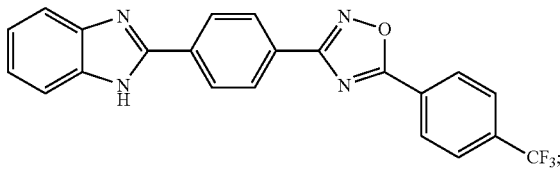

3-(4-(1H-Benzo[d]imidazol-2-yl)phenyl)-5-
(4-(trifluoromethyl)phenyl)-1,2,4-oxadiazole
(1e)

-continued

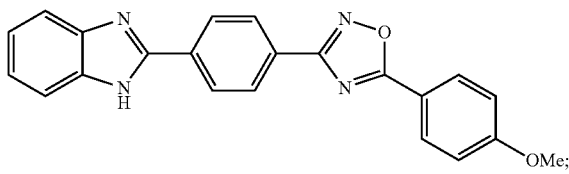

3-(4-(1H-Benzo[d]imidazol-2-yl)phenyl)-5-
(4-methoxyphenyl)-1,2,4-oxadiazole
(1f)

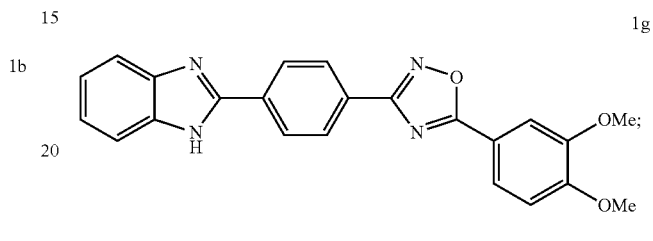

3-(4-(1H-Benzo[d]imidazol-2-yl)phenyl)-5-
(3,4-dimethoxyphenyl)-1,2,4-oxadiazole
(1g)

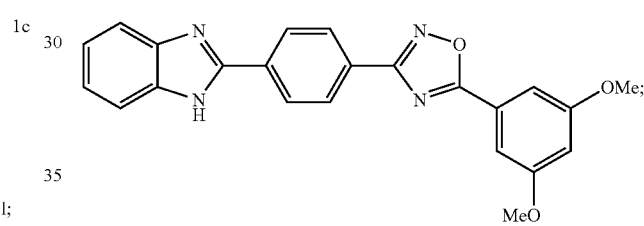

3-(4-(1H-Benzo[d]imidazol-2-yl)phenyl)-5-
(3,5-dimethoxyphenyl)-1,2,4-oxadiazole
(1h)

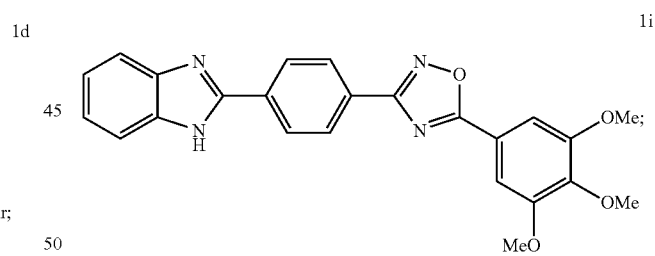

3-(4-(1H-Benzo[d]imidazol-2-yl)phenyl)-5-
(3,4,5-trimethoxyphenyl)-1,2,4-oxadiazole
(1i)

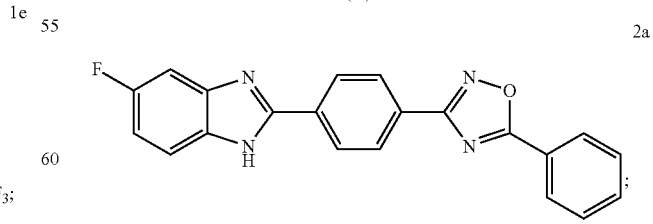

3-(4-(5-Fluoro-1H-benzo[d]imidazol-2-yl)phenyl)-5-
phenyl-1,2,4-oxadiazole
(2a)

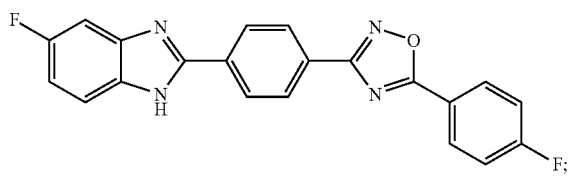

3-(4-(5-Fluoro-1H-benzo[d]imidazol-2-yl)phenyl)-5-
(4-fluorophenyl)-1,2,4-oxadiazole
(2b)

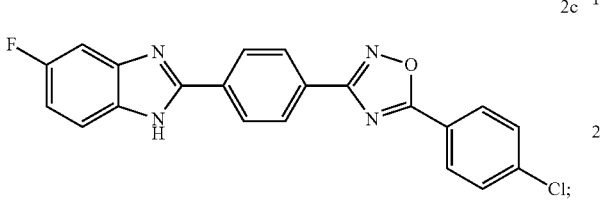

5-(4-Chlorophenyl)-3-(4-(5-fluoro-1H-benzo[d]imidazol-2-yl)
phenyl)-1,2,4-oxadiazole
(2c)

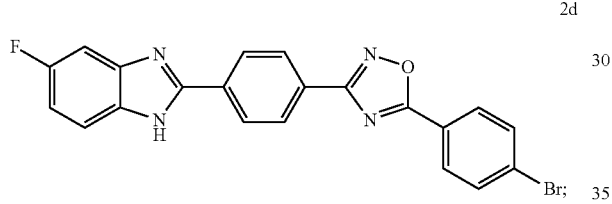

5-(4-Bromophenyl)-3-(4-(5-fluoro-1H-benzo[d]imidazol-2-yl)
phenyl)-1,2,4-oxadiazole
(2d)

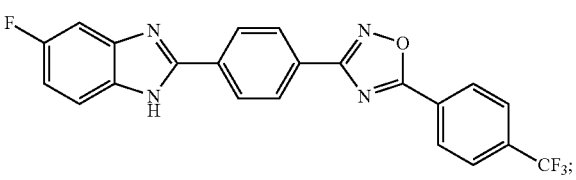

3-(4-(5-Fluoro-1H-benzo[d]imidazol-2-yl)phenyl)-5-
(4-(trifluoromethyl)phenyl)-1,2,4-oxadiazole
(2e)

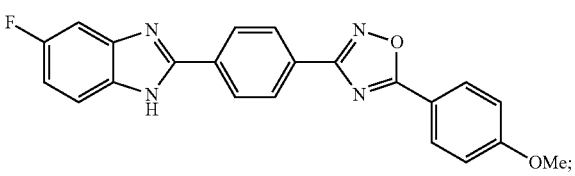

3-(4-(5-Fluoro-1H-benzo[d]imidazol-2-yl)phenyl)-5-
(4-methoxyphenyl)-1,2,4-oxadiazole
(2f)

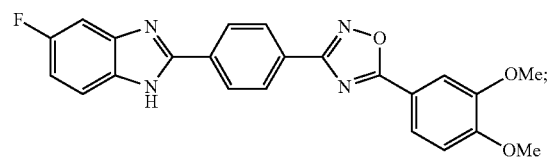

5-(3,4-Dimethoxyphenyl)-3-(4-(5-fluoro-1H-benzo[d]imidazol-2-
yl)phenyl)-1,2,4-oxadiazole
(2g)

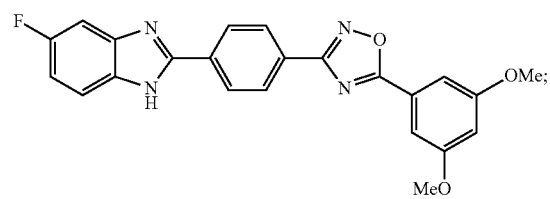

5-(3,5-Dimethoxyphenyl)-3-(4-(5-fluoro-1H-benzo[d]imidazol-2-
yl)phenyl)-1,2,4-oxadiazole
(2h)

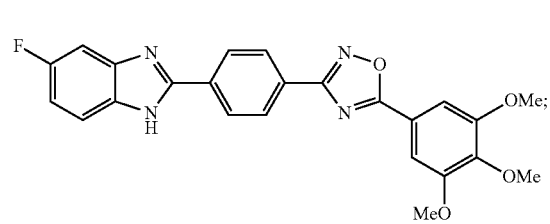

3-(4-(5-Fluoro-1H-benzo[d]imidazol-2-yl)phenyl)-5-(3,4,5-
trimethoxyphenyl)-1,2,4-oxadiazole
(2i)

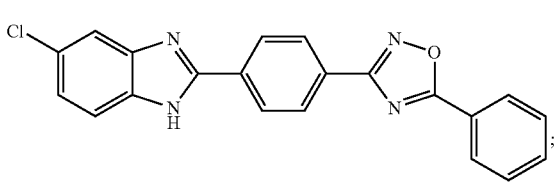

3-(4-(5-Chloro-1H-benzo[d]imidazol-2-yl)phenyl)-5-phenyl-
1,2,4-oxadiazole
(3a)

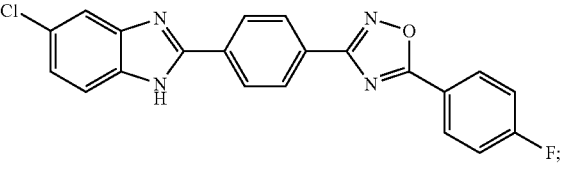

3-(4-(5-Chloro-1H-benzo[d]imidazol-2-yl)phenyl)-5-(4-fluorophenyl)-
1,2,4-oxadiazole
(3b)

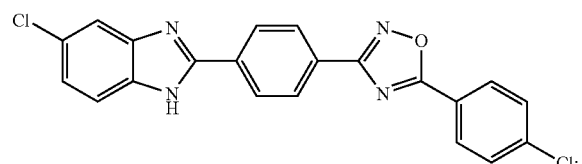

3-(4-(5-Chloro-1H-benzo[d]imidazol-2-yl)phenyl)-5-(4-chlorophenyl)-
1,2,4-oxadiazole
(3c)

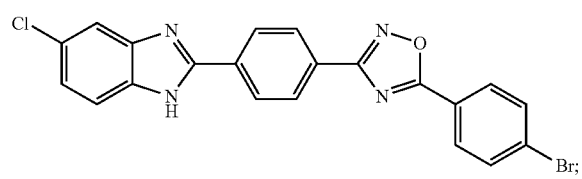

3-(4-(5-Chloro-1H-benzo[d]imidazol-2-yl)phenyl)-5-(4-bromophenyl)-
1,2,4-oxadiazole
(3d)

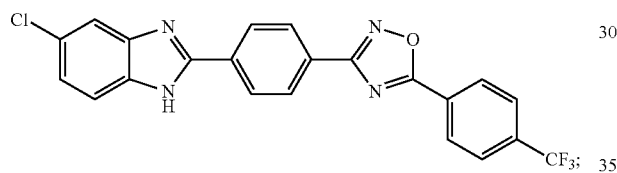

3-(4-(5-Chloro-1H-benzo[d]imidazol-2-yl)phenyl)-5-(4-
(trifluoromethyl)phenyl)-
1,2,4-oxadiazole
(3e)

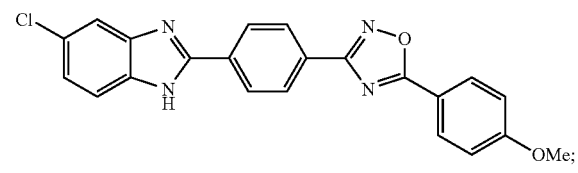

3-(4-(5-Chloro-1H-benzo[d]imidazol-2-yl)phenyl)-5-(4-methoxyphenyl)-
1,2,4-oxadiazole
(3f)

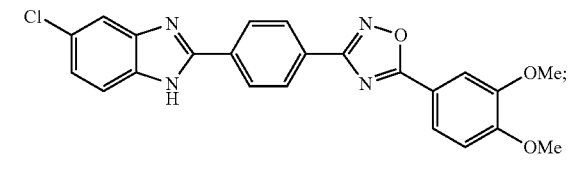

3-(4-(5-Chloro-1H-benzo[d]imidazol-2-yl)phenyl)-5-(3,4-
dimethoxyphenyl)-
1,2,4-oxadiazole
(3g)

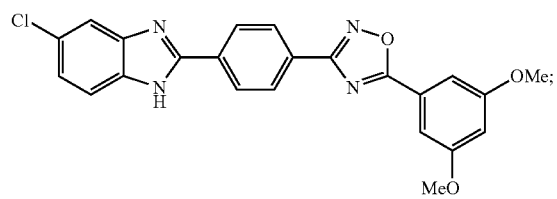

3-(4-(5-Chloro-1H-benzo[d]imidazol-2-yl)phenyl)-5-(3,5-
dimethoxyphenyl)-
1,2,4-oxadiazole
(3h)

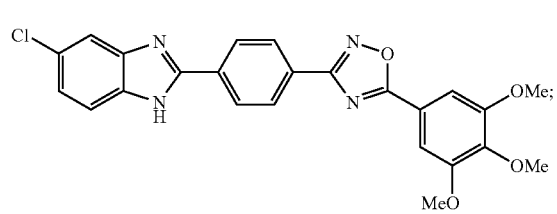

3-(4-(5-Chloro-1H-benzo[d]imidazol-2-yl)phenyl)-5-(3,4,5-
trimethoxyphenyl)-
1,2,4-oxadiazole
(3i)

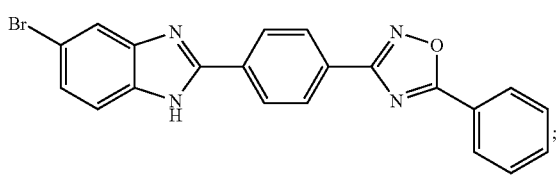

3-(4-(5-Bromo-1H-benzo[d]imidazol-2-yl)phenyl)-5-phenyl-
1,2,4-oxadiazole
(4a)

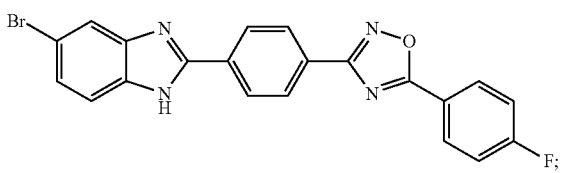

3-(4-(5-Bromo-1H-benzo[d]imidazol-2-yl)phenyl)-5-(4-fluorophenyl)-
1,2,4-oxadiazole
(4b)

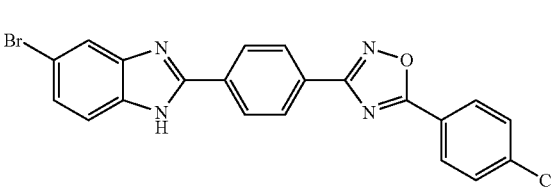

3-(4-(5-Bromo-1H-benzo[d]imidazol-2-yl)phenyl)-5-(4-chlorophenyl)-
1,2,4-oxadiazole
(4c)

-continued

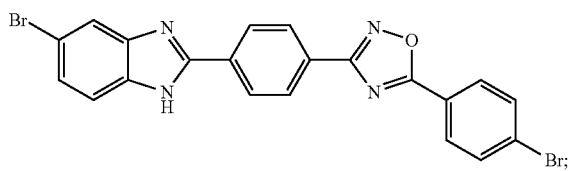

3-(4-(5-Bromo-1H-benzo[d]imidazol-2-yl)phenyl)-5-(4-bromophenyl)-
1,2,4-oxadiazole
(4d)

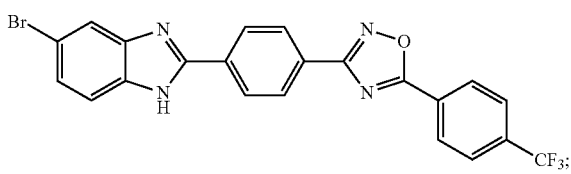

3-(4-(5-Bromo-1H-benzo[d]imidazol-2-yl)phenyl)-5-(4-
(trifluoromethyl)phenyl)-
1,2,4-oxadiazole
(4e)

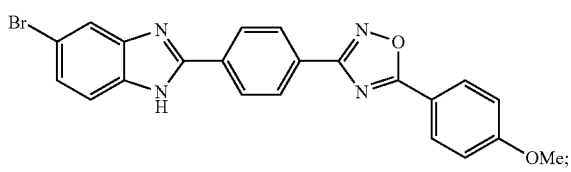

3-(4-(5-Bromo-1H-benzo[d]imidazol-2-yl)phenyl)-5-(4-methoxyphenyl)-
1,2,4-oxadiazole
(4f)

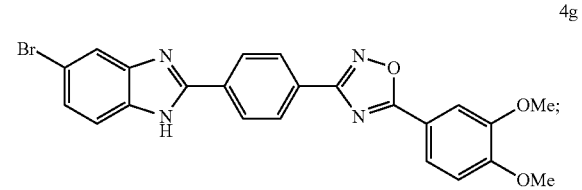

3-(4-(5-Bromo-1H-benzo[d]imidazol-2-yl)phenyl)-5-(3,4-
dimethoxyphenyl)-
1,2,4-oxadiazole
(4g)

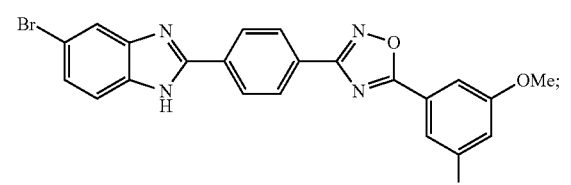

3-(4-(5-Bromo-1H-benzo[d]imidazol-2-yl)phenyl)-5-(3,5-
dimethoxyphenyl)-
1,2,4-oxadiazole
(4h)

-continued

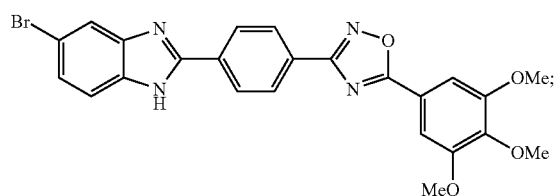

3-(4-(5-Bromo-1H-benzo[d]imidazol-2-yl)phenyl)-5-(3,4,5-
trimethoxyphenyl)-
1,2,4-oxadiazole
(4i)

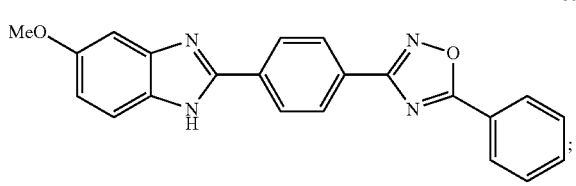

3-(4-(5-Methoxy-1H-benzo[d]imidazol-2-yl)phenyl)-5-phenyl-
1,2,4-oxadiazole
(5a)

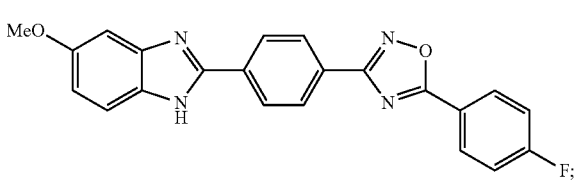

5-(4-Fluorophenyl)-3-(4-(5-methoxy-1H-benzo[d]imidazol-2-yl)phenyl-
1,2,4-oxadiazole
(5b)

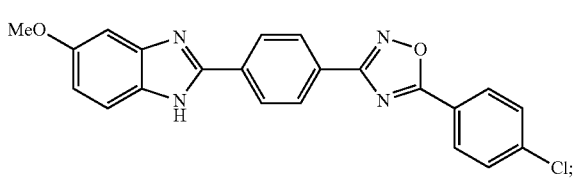

5-(4-Chlorophenyl)-3-(4-(5-methoxy-1H-benzo[d]imidazol-2-yl)phenyl)-
1,2,4-oxadiazole
(5c)

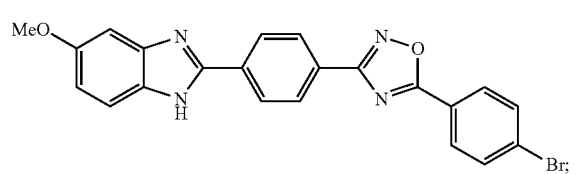

5-(4-Bromophenyl)-3-(4-(5-methoxy-1H-benzo[d]imidazol-2-yl)phenyl)-
1,2,4-oxadiazole
(5d)

-continued

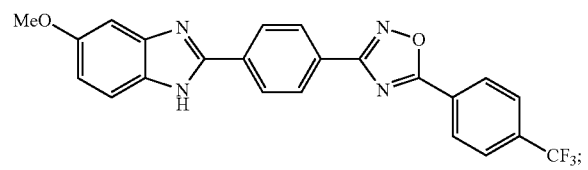

3-(4-(5-Methoxy-1H-benzo[d]imidazol-2-yl)phenyl-5-(4-(trifluoromethyl)phenyl)-1,2,4-oxadiazole
(5e)

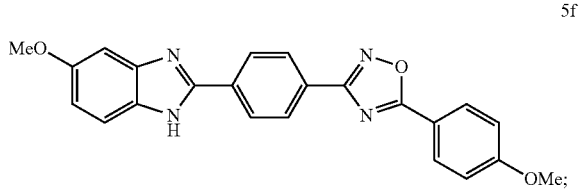

3-(4-(5-Methoxy-1H-benzo[d]imidazol-2-yl)phenyl)-5-(4-methoxyphenyl)-1,2,4-oxadiazole
(5f)

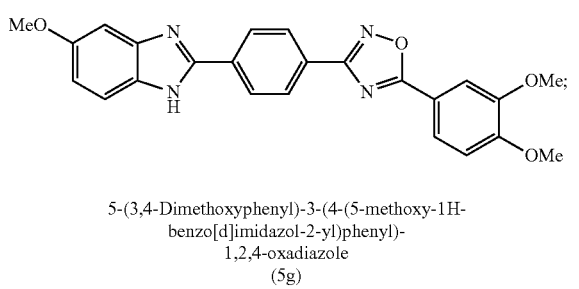

5-(3,4-Dimethoxyphenyl)-3-(4-(5-methoxy-1H-benzo[d]imidazol-2-yl)phenyl)-1,2,4-oxadiazole
(5g)

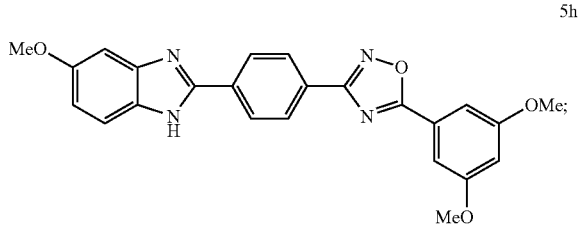

5-(3,5-Dimethoxyphenyl)-3-(4-(5-methoxy-1H-benzo[d]imidazol-2-yl)phenyl)-1,2,4-oxadiazole
(5h)

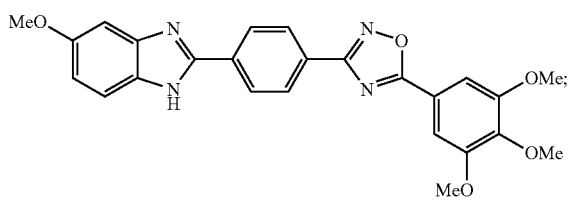

3-(4-(5-Methoxy-1H-benzo[d]imidazol-2-yl)phenyl)-5-(3,4,5-trimethoxyphenyl)-1,2,4-oxadiazole
(5i)

-continued

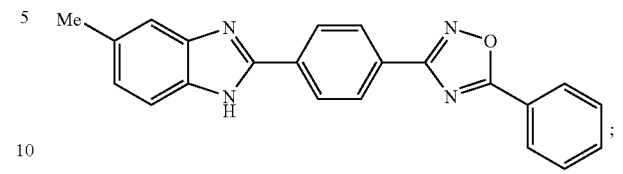

3-(4-(5-Methyl-1H-benzo[d]imidazol-2-yl)phenyl)-5-phenyl-1,2,4-oxadiazole
(6a)

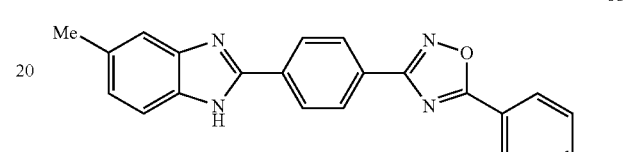

5-(4-Fluorophenyl)-3-(4-(5-methyl-1H-benzo[d]imidazol-2-yl)phenyl)-1,2,4-oxadiazole
(6b)

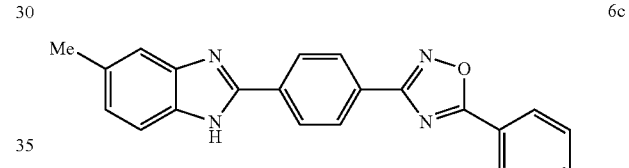

5-(4-Chlorophenyl)-3-(4-(5-methyl-1H-benzo[d]imidazol-2-yl)phenyl)-1,2,4-oxadiazole
(6c)

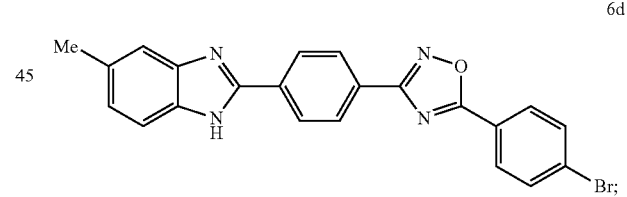

5-(4-Bromophenyl)-3-(4-(5-methyl-1H-benzo[d]imidazol-2-yl)phenyl)-1,2,4-oxadiazole
(6d)

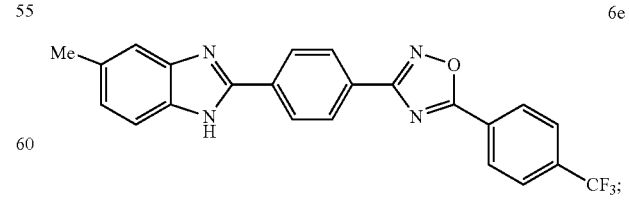

3-(4-(5-Methyl-1H-benzo[d]imidazol-2-yl)phenyl)-5-(4-(trifluoromethyl)phenyl)-1,2,4-oxadiazole
(6e)

-continued

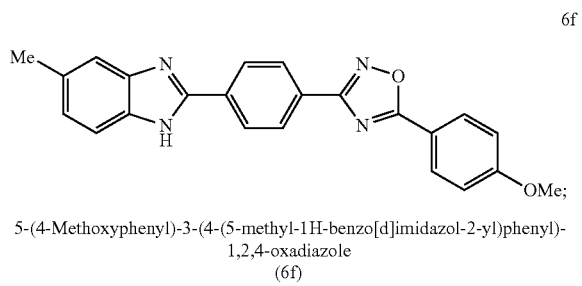

5-(4-Methoxyphenyl)-3-(4-(5-methyl-1H-benzo[d]imidazol-2-yl)phenyl)-1,2,4-oxadiazole
(6f)

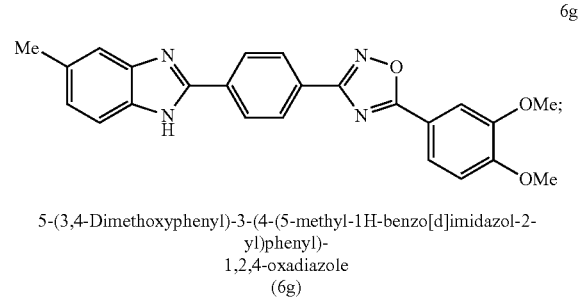

5-(3,4-Dimethoxyphenyl)-3-(4-(5-methyl-1H-benzo[d]imidazol-2-yl)phenyl)-1,2,4-oxadiazole
(6g)

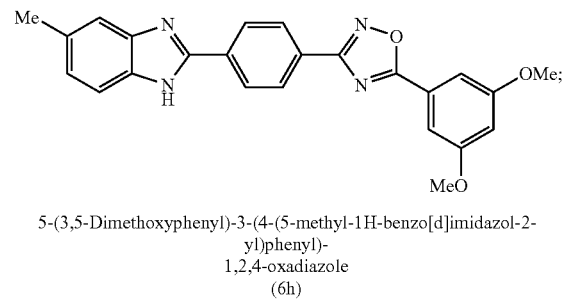

5-(3,5-Dimethoxyphenyl)-3-(4-(5-methyl-1H-benzo[d]imidazol-2-yl)phenyl)-1,2,4-oxadiazole
(6h)

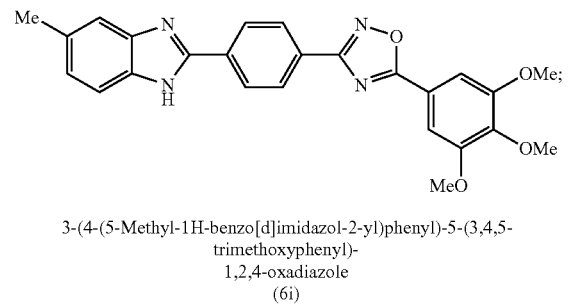

3-(4-(5-Methyl-1H-benzo[d]imidazol-2-yl)phenyl)-5-(3,4,5-trimethoxyphenyl)-1,2,4-oxadiazole
(6i)

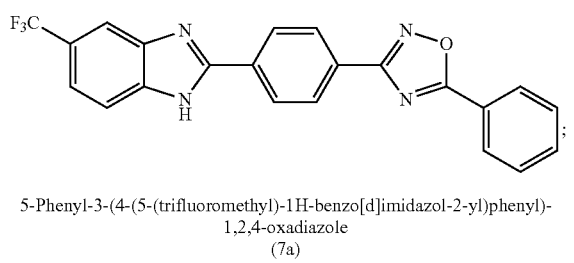

5-Phenyl-3-(4-(5-(trifluoromethyl)-1H-benzo[d]imidazol-2-yl)phenyl)-1,2,4-oxadiazole
(7a)

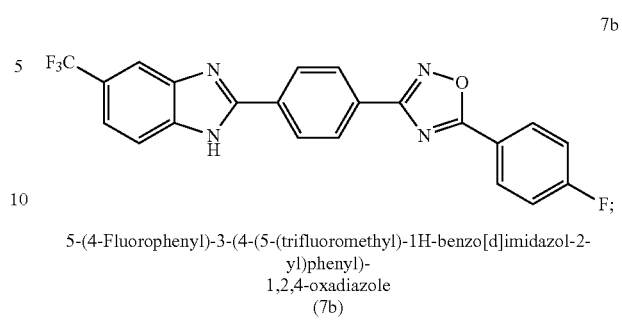

5-(4-Fluorophenyl)-3-(4-(5-(trifluoromethyl)-1H-benzo[d]imidazol-2-yl)phenyl)-1,2,4-oxadiazole
(7b)

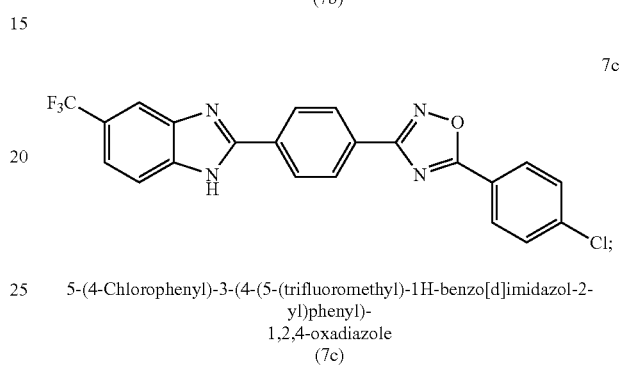

5-(4-Chlorophenyl)-3-(4-(5-(trifluoromethyl)-1H-benzo[d]imidazol-2-yl)phenyl)-1,2,4-oxadiazole
(7c)

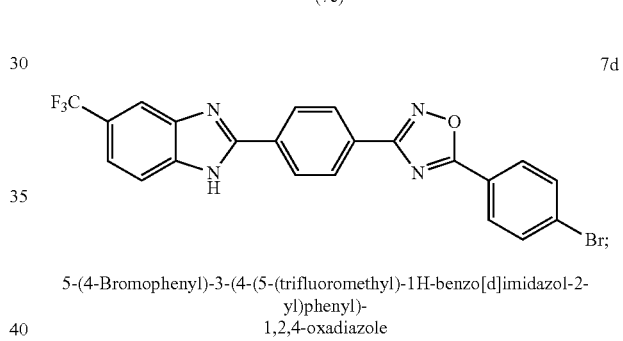

5-(4-Bromophenyl)-3-(4-(5-(trifluoromethyl)-1H-benzo[d]imidazol-2-yl)phenyl)-1,2,4-oxadiazole
(7d)

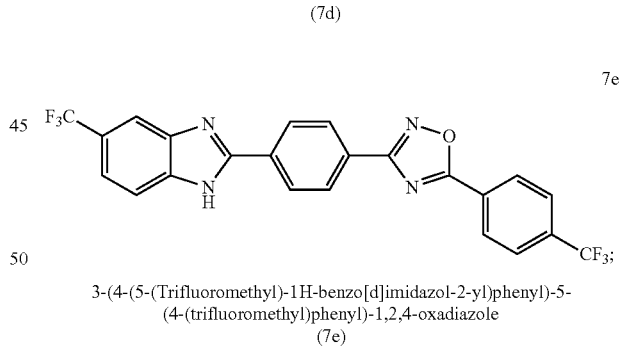

3-(4-(5-(Trifluoromethyl)-1H-benzo[d]imidazol-2-yl)phenyl)-5-(4-(trifluoromethyl)phenyl)-1,2,4-oxadiazole
(7e)

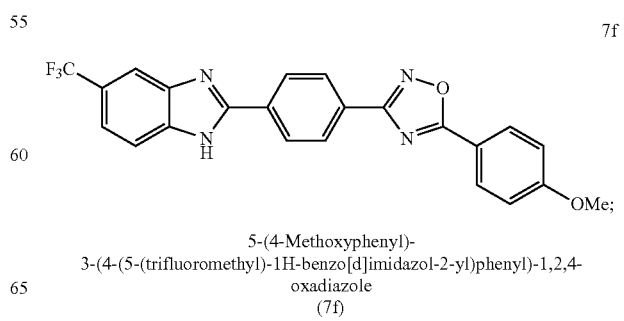

5-(4-Methoxyphenyl)-3-(4-(5-(trifluoromethyl)-1H-benzo[d]imidazol-2-yl)phenyl)-1,2,4-oxadiazole
(7f)

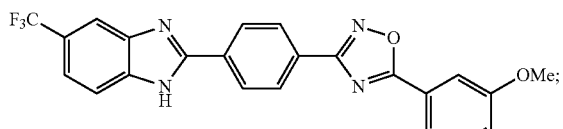

5-(3,4-Dimethoxyphenyl)-3-(4-(5-trifluoromethyl)-1H-benzo[d]
imidazol-2-yl)phenyl)-
1,2,4-oxadiazole
(7g)

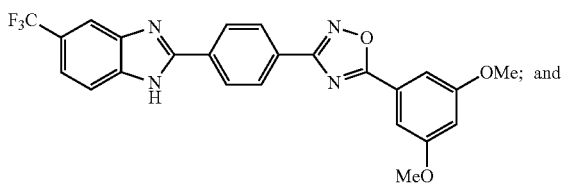

5-(3,5-Dimethoxyphenyl)-3-(4-(5-trifluoromethyl)-1H-benzo[d]
imidazol-2-yl)phenyl)-
1,2,4-oxadiazole
(7h)

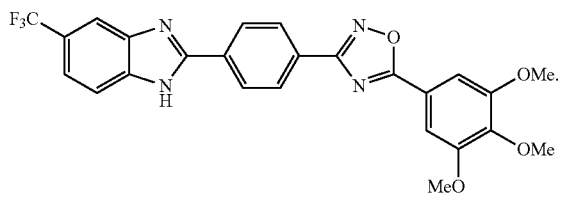

3-(4-(5-Trifluoromethyl)-1H-benzo[d]
imidazol-2-yl)phenyl)-5-(3,4,5-trimethoxyphenyl)
1,2,4-oxadiazole
(7i)

In yet another embodiment of the present invention, said compound is for use in treatment of cancer.

In another embodiment of the present invention, the compound is for use in the treatment of cancer selected from the group consisting of leukemia, melanoma, ovarian, colon, CNS, prostate and breast cancer.

In yet another embodiment of the present invention, said compound 5i and 2i exhibit cytotoxic activity against SR (leukemia cell line) and BT-549 (breast cancer cell line) with $GI_{50}$ values of 0.71 and 0.52 μM respectively.

In yet another embodiment, present invention provides a process for the preparation of compound of general formula A, the process comprising the steps of:

i. reacting a compound of formula 11 (a-i)

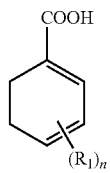

11 (a-i)

wherein $R_1$ is selected from the group consisting of H; 4-F; 4-Cl; 4-Br; 4-CF$_3$; 4-OMe; 3,4-OMe; 3,5-OMe and 3,4,5-OMe, n is an integer ranging from 1-3. with carbonyldiimidazole in a ratio ranging between 1:1 to 1:3 in dry DMF under nitrogen atmosphere followed by stirring at a temperature in the range of 35-37° C. for a period in the range of 50 to 60 minutes to obtain a first mixture;

ii. adding amidoximes of formula 10a-g to the first mixture obtained in step (i) in a ratio ranging between 1:1 to 1:1.5, followed by heating at a temperature in the range of 110-115° C. for a period in the range of 16-18 hours to obtain a second mixture; and

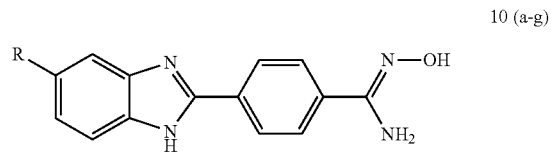

10 (a-g)

wherein R is selected from the group consisting of H, F, Cl, Br, OMe, Me and CF$_3$, iii. cooling the second mixture obtained in step (ii) at a temperature in the range of 20 to 25° C., pouring into ice-cold water, extracting, washing, drying, filtering and concentrating in vacuum followed by purifying by column chromatography to obtain the compound of general formula A.

In yet another embodiment, present invention provides a pharmaceutical composition comprising therapeutically effective amount of compound of general formula A, optionally along with one or more pharmaceutically acceptable carriers, additives, lubricants and diluents.

DETAILED DESCRIPTION OF THE INVENTION

The present invention provides a 3-[4-(1H-Benzo[d]imidazol-2-yl)phenyl]-5-phenyl-1,2,4-oxadiazoles of general formula A General formula A

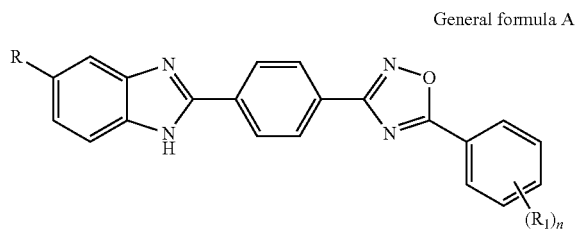

wherein
R is selected from the group consisting of H, F, Cl, Br, OMe, Me and CF$_3$,
$R_1$ is selected from the group consisting of H, 4-F, 4-Cl, 4-Br, 4-CF$_3$, 4-OMe, 3,4-OMe, 3,5-OMe and 3,4,5-OMe, and
n is an integer ranging from 1-3.

The starting o-phenylenediamines of formula 8(a-g), 4-cyanobenzaldehyde (7) and aromatic carboxylic acids of formula 11(a-i) are commercially available and the 3-(4-(1H-benzo[d]imidazol-2-yl) phenyl)-5-phenyl-1,2,4-oxadiazole derivatives of formula 1a-i to 7a-i have been prepared as illustrated in the Scheme 1.

Scheme 1
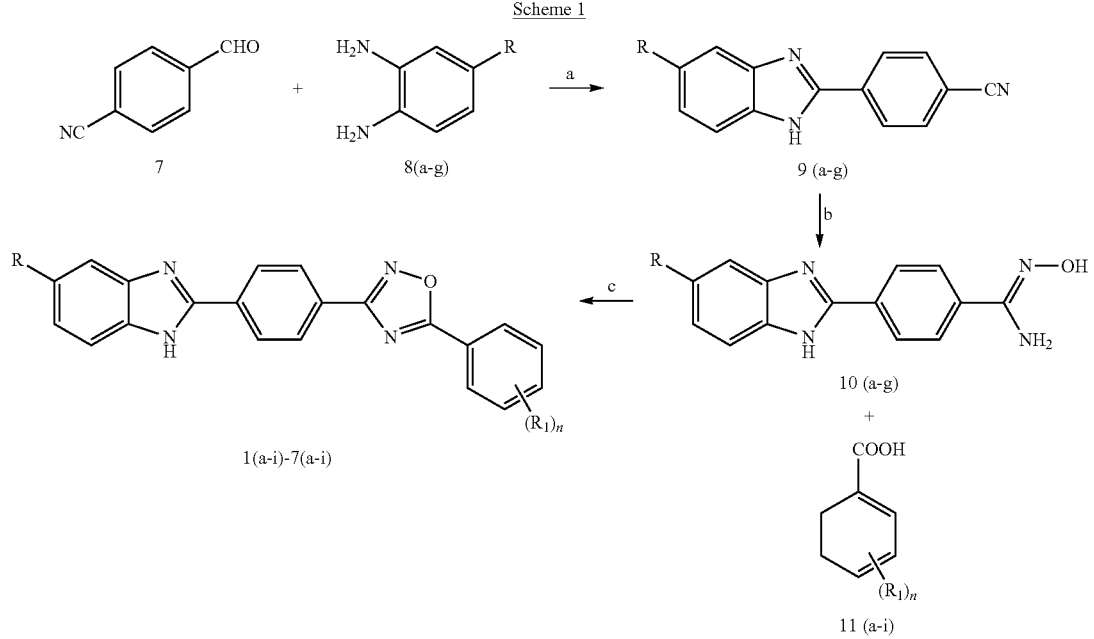
| Formula | R |
|---|---|
| 8a | H |
| 8b | F |
| 8c | Cl |
| 8d | Br |
| 8e | OMe |
| 8f | Me |
| 8g | CF$_3$ |
| 9a | H |
| 9b | F |
| 9c | Cl |
| 9d | Br |
| 9e | OMe |
| 9f | Me |
| 9g | CF$_3$ |
| 10a | H |
| 10b | F |
| 10c | Cl |
| 10d | Br |
| 10e | OMe |
| 10f | Me |
| 10g | CF$_3$ |
| Formula | R$_1$ | n |
|---|---|---|
| 11a | 4-H | 1 |
| 11b | 4-F | 1 |
| 11c | 4-Cl | 1 |
| 11d | 4-Br | 1 |
| 11e | 4-CF$_3$ | 1 |
| 11f | 4-OMe | 1 |
| 11g | 3,4-OMe | 2 |
| 11h | 3,5-OMe | 2 |
| 11i | 3,4,5-OMe | 3 |
| SI No. | Formula | R | R$_1$ | n |
|---|---|---|---|---|
| 1 | 1a | H | 4-H | 1 |
| 2 | 1b | H | 4-F | 1 |
| 3 | 1c | H | 4-Cl | 1 |
| 4 | 1d | H | 4-Br | 1 |
| 5 | 1e | H | 4-CF$_3$ | 1 |
| 6 | 1f | H | 4-OMe | 1 |
| 7 | 1g | H | 3,4-OMe | 2 |
| 8 | 1h | H | 3,5-OMe | 2 |
| 9 | 1i | H | 3,4,5-OMe | 3 |
| 10 | 2a | F | 4-H | 1 |
| 11 | 2b | F | 4-F | 1 |
| 12 | 2c | F | 4-Cl | 1 |
| 13 | 2d | F | 4-Br | 1 |
| 14 | 2e | F | 4-CF$_3$ | 1 |
| 15 | 2f | F | 4-OMe | 1 |
| 16 | 2g | F | 3,4-OMe | 2 |
| 17 | 2h | F | 3,5-OMe | 2 |
| 18 | 2i | F | 3,4,5-OMe | 3 |
| 19 | 3a | Cl | 4-H | 1 |
| 20 | 3b | Cl | 4-F | 1 |
| 21 | 3c | Cl | 4-Cl | 1 |
| 22 | 3d | Cl | 4-Br | 1 |
| 23 | 3e | Cl | 4-CF$_3$ | 1 |
| 24 | 3f | Cl | 4-OMe | 1 |
| 25 | 3g | Cl | 3,4-OMe | 2 |
| 26 | 3h | Cl | 3,5-OMe | 2 |
| 27 | 3i | Cl | 3,4,5-OMe | 3 |
| 28 | 4a | Br | 4-H | 1 |
| 29 | 4b | Br | 4-F | 1 |
| 30 | 4c | Br | 4-Cl | 1 |

| SI No. | Formula | R | $R_1$ | n |
|---|---|---|---|---|
| 31 | 4d | Br | 4-Br | 1 |
| 32 | 4e | Br | 4-$CF_3$ | 1 |
| 33 | 4f | Br | 4-OMe | 1 |
| 34 | 4g | Br | 3,4-OMe | 2 |
| 35 | 4h | Br | 3,5-OMe | 2 |
| 36 | 4i | Br | 3,4,5-OMe | 3 |
| 37 | 5a | OMe | 4-H | 1 |
| 38 | 5b | OMe | 4-F | 1 |
| 39 | 5c | OMe | 4-Cl | 1 |
| 40 | 5d | OMe | 4-Br | 1 |
| 41 | 5e | OMe | 4-$CF_3$ | 1 |
| 42 | 5f | OMe | 4-OMe | 1 |
| 43 | 5g | OMe | 3,4-OMe | 2 |
| 44 | 5h | OMe | 3,5-OMe | 2 |
| 45 | 5i | OMe | 3,4,5-OMe | 3 |
| 46 | 6a | Me | 4-H | 1 |
| 47 | 6b | Me | 4-F | 1 |
| 48 | 6c | Me | 4-Cl | 1 |
| 49 | 6d | Me | 4-Br | 1 |
| 50 | 6e | Me | 4-$CF_3$ | 1 |
| 51 | 6f | Me | 4-OMe | 1 |
| 52 | 6g | Me | 3,4-OMe | 2 |
| 53 | 6h | Me | 3,5-OMe | 2 |
| 54 | 6i | Me | 3,4,5-OMe | 3 |
| 55 | 7a | $CF_3$ | 4-H | 1 |
| 56 | 7b | $CF_3$ | 4-F | 1 |
| 57 | 7c | $CF_3$ | 4-Cl | 1 |
| 58 | 7d | $CF_3$ | 4-Br | 1 |
| 59 | 7e | $CF_3$ | 4-$CF_3$ | 1 |
| 60 | 7f | $CF_3$ | 4-OMe | 1 |
| 61 | 7g | $CF_3$ | 3,4-OMe | 2 |
| 62 | 7h | $CF_3$ | 3,5-OMe | 2 |
| 63 | 7i | $CF_3$ | 3,4,5-OMe | 3 |

Scheme 1 represents synthesis of 3-(4-(1H-benzo[d]imidazol-2-yl)phenyl)-5-phenyl-1,2,4-oxadiazole derivatives (1a-i to 7a-i) of general formula A wherein reagents and conditions: (a) EtOH, $H_2O$, $Na_2S_2O_5$, reflux, 5 h; (b) EtOH, $H_2O$, $NH_2OH.HCl$, NaOH, reflux, 18 h; (c) DMF, CDI, aromatic carboxylic acids (11a-i), 0° C. to 30° C., 3 h then 110° C. 18 h.

i. The nitrile compounds of formula 9(a-g) were prepared according to the following method. To a mixture of appropriate o-phenylenediamines of formula 8 (a-g) (0.5 mmol) and 4-cyano benzaldehyde (7) (0.5 mmol) in ethanol was added a solution of $Na_2S_2O_5$ (4 mmol) in $H_2O$ (1.6 mL). The resulting mixture was stirred at reflux for 4 h, after completion of reaction; the solution was poured onto crushed ice. The resulting solid was filtered, washed with cold water, dried and recrystallized from ethanol to afford compounds of formula 9(a-g). (Singhal, N.; Johar, M.; Lown, J. W.; Sondhi, S. M. *Phosphorous, Sulfur Silicon Relat. Elem.* 2001, 174, 81)

ii. To a solution of appropriate benzonitrile of formula 9 (a-g) (10 mmol) in ethanol (5 ml) was added hydroxylamine hydrochloride (11 mmol, 764 mg) and sodium hydroxide (11 mmol, 444 mg), each dissolved in water (10 mL) sequentially, over a period of 20 min while maintaining the temperature at 0° C. Then the resulting mixture was allowed to reflux with stirring for 18 h. The pH of the solution was adjusted to 2 with 1N HCl and the aqueous phase was washed with ethylacetate (2×25 mL). Upon cooling (0° C.) and neutralization with sodium bi carbonate gave precipitate which was filtered, washed and dried to afford pure amidoximes of formula 10(a-g).

iii. To a solution of appropriate carboxylic acid of formula 11 (a-i) (0.5 mmol) in dry DMF (3 mL) was added carbonyl diimidazole (0.6 mmol) under nitrogen atmosphere and the reaction mixture was stirred at 35-37° C. for 1 h. Then appropriate amidoxime of formula 10 (a-g) (0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish pure 1,2,4-oxadiazoles of formula 1a-i to 7a-i in moderate yields.

All the 3-[4-(1H-benzo[d]imidazol-2-yl)phenyl]-5-phenyl-1,2,4-oxadiazole derivatives were synthesized and purified by column chromatography using solvent selected from the group consisting of ethyl acetate and hexane or combination thereof.

These analogues of 3-[4-(1H-benzo[d]imidazol-2-yl)phenyl]-5-phenyl-1,2,4-oxadiazole derivatives have shown promising anticancer activity in various cancer cell lines.

EXAMPLES

The following examples are given by way of illustration and therefore should not be construed to limit the scope of present invention.

Example 1

4-(1H-benzo[d]imidazol-2-yl)benzonitrile 9a

To a mixture of appropriate o-phenylenediamine 8a (590 mg, 5 mmol) and 4-cyano benzaldehyde 7 (655 mg, 5 mmol) in 5 ml ethanol was added a solution of $Na_2S_2O_5$ (2.80 g, 40 mmol) in $H_2O$ (1.8 mL). The resulting mixture was stirred at 80° C. for 4 h, after completion of reaction, the solution was poured onto crushed ice. The resulting solid was filtered, washed with cold water, dried and recrystallized from 3 ml ethanol to afford compound 9a as off white solid 810 mg in 72% yield. $^1$H NMR (300 MHz, $CDCl_3$) δ 7.83-7.68 (m, 4H), 7.66-7.53 (m, 3H), 7.27 (d, J=10.2 Hz, 2H); MS (ESI): m/z 220 [M+H]+.

Example 2

((Z)-4-(1H-benzo[d]imidazol-2-yl)-N'-hydroxybenzimidamide) 10a

To a solution of compound 9a (2.19 g, 10 mmol) in ethanol (10 ml) was added Hydroxylamine hydrochloride (11 mmol, 764 mg) and sodium hydroxide (11 mmol, 444 mg), each dissolved in water (10 mL) sequentially, over a period of 20 min while maintaining the temperature at 0-5° C. Then the resulting mixture was allowed to reflux at 80° C. with stirring for 18 h. The pH of the solution was adjusted to 2 with 1N HCl and the aqueous phase was washed with ethylacetate (2×25 mL). Upon cooling (0° C.) and neutralization with sodium bi carbonate gave precipitate which was filtered, washed and dried to afford 10a as off white solid 1.87 g, in 74.2% yield. $^1$H NMR (300 MHz, DMSO-d6) δ 7.86-7.71 (m, 1H), 7.65-7.44 (m, 2H), 7.29 (d, J=7.8 Hz, 1H), 7.22-7.12 (m, 1H), 2.38 (s, 1H), 1.22-1.08 (m, 1H). MS (ESI): m/z 253 [M+H]$^+$.

Example 3

(3-(4-(1H-Benzo[d]imidazol-2-yl)phenyl)-5-phenyl-1,2,4-oxadiazole) 1a

To a solution of benzoic acid (11a, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(1H-Benzo[d]imidazol-2-yl)-N'-hydroxybenzimidamide) (10a, 152 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 1a as off white solid 121 mg, in 59% yield. $^1$H NMR (300 MHz, CDCl$_3$) δ 5.30 (bs, 1H), 7.11 (t, 1H, J=7.29 Hz), 7.16-7.25 (m, 4H), 7.58 (d, 2H, J=8.12 Hz), 7.89 (d, 2H, J=8.12 Hz), 8.24 (dd, 4H, J=8.32, 5.65 Hz); MS (ESI): m/z 339 [M+H]$^+$.

Example 4

(3-(4-(1H-Benzo[d]imidazol-2-yl)phenyl)-5-(4-fluorophenyl)-1,2,4-oxadiazole) 1b

To a solution of 4-flouro benzoic acid (11b, 70 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(1H-Benzo[d]imidazol-2-yl)-N'-hydroxybenzimidamide) (10a, 152 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 1b as off white solid 115 mg, in 53% yield. $^1$H NMR (300 MHz, CDCl$_3$) δ 5.29 (bs, 1H), 7.16-7.24 (m, 2H), 7.50-7.59 (m, 2H), 7.56 (d, 2H, J=8.23 Hz), 7.92 (d, 2H, J=8.23 Hz), 8.19-8.30 (m, 4H); MS (ESI): m/z 357 [M+H]$^+$.

Example 5

(3-(4-(1H-Benzo[d]imidazol-2-yl)phenyl)-5-(4-chlorophenyl)-1,2,4-oxadiazole) 1c

To a solution of 4-chloro benzoic acid (11c, 78 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(1H-Benzo[d]imidazol-2-yl)-N'-hydroxybenzimidamide) (10a, 152 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 1c as off white solid 127 mg, in 56% yield. $^1$H NMR (500 MHz, CDCl$_3$) δ 5.32 (bs, 1H), 7.18-7.24 (m, 2H), 7.52-7.63 (m, 4H), 7.87 (d, 2H, J=8.12 Hz), 8.18-8.30 (dd, 4H, J=8.30, 5.61 Hz); MS (ESI): m/z 373 [M+H]$^+$.

Example 6

(3-(4-(1H-Benzo[d]imidazol-2-yl)phenyl)-5-(4-methoxyphenyl)-1,2,4-oxadiazole) 1f To a solution of 4-methoxy benzoic acid (11f, 176 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(1H-Benzo[d]imidazol-2-yl)-N-hydroxybenzimidamide) (10a, 152 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 1f as off white solid 108 mg, in 48.6% yield. $^1$H NMR (300 MHz, CDCl$_3$) δ 3.84 (s, 3H), 5.29 (bs, 1H), 6.89 (d, 2H, J=8.68 Hz), 7.21-7.42 (m, 4H), 7.81 (d, 2H, J=8.12 Hz), 8.19-8.28 (m, 4H); MS (ESI): m/z 369 [M+H]$^+$.

Example 7

(3-(4-(1H-Benzo[d]imidazol-2-yl)phenyl)-5-(3,4,5-trimethoxyphenyl)-1,2,4-oxadiazole) 1i To a solution of 3,4,5-trimethoxy benzoic acid (11i, 106 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(1H-Benzo[d]imidazol-2-yl)-N'-hydroxybenzimidamide) (10a, 152 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 1i as off white solid 146 mg, in 56.5% yield. $^1$H NMR (300 MHz, CDCl$_3$) δ 3.87 (s, 3H), 3.91 (s, 6H), 5.27 (bs, 1H), 7.04 (s, 2H), 7.20-7.31 (m, 2H), 7.41-7.49 (m, 2H), 8.19-8.28 (dd, 4H, J=8.30, 7.93 Hz); MS (ESI): m/z 430 [M+H]$^+$.

Example 8

(3-(4-(5-Fluoro-1H-benzo[d]imidazol-2-yl)phenyl)-5-phenyl-1,2,4-oxadiazole) 2a

To a solution of benzoic acid (11a, 61 mg, 0.5 mmol) in dry DMF (3 mL) was added carbonyl diimidazole (97 mg, 0.6 mmol) under nitrogen atmosphere and the reaction mixture was stirred at 37° C. for 1 h. Then 9(Z)-4-(5-Fluoro-1H-benzo[d]imidazol-2-yl)-N'-hydroxybenzimidamide) (10b, 162 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 2a as off white solid 127 mg, in 59.6% yield. $^1$H NMR (300 MHz, CDCl$_3$) δ 5.31 (bs, 1H), 7.02 (d, 1H, J=7.29 Hz), 7.32-7.41 (m, 4H) 7.59 (d, 1H, J=7.29 Hz), 7.79 (d, 2H, J=8.12 Hz), 8.19-8.30 (m, 4H); MS (ESI): m/z 357 [M+H]$^+$.

Example 9

(3-(4-(5-Fluoro-1H-benzo[d]imidazol-2-yl)phenyl)-5-(4-fluorophenyl)-1,2,4-oxadiazole) 2b To a solution of 4-flouro benzoic acid (11b, 70 mg, 0.5 mmol) in dry DMF (3 mL) was added carbonyl diimidazole (97 mg, 0.6 mmol) under nitrogen atmosphere and the reaction mixture was stirred at 37° C. for 1 h. Then 9(Z)-4-(5-Fluoro-1H-benzo[d]imidazol-2-yl)-N'-hydroxybenzimidamide) (10b, 162 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 2b as off white solid 131 mg, in 58.6% yield. $^1$H NMR (300 MHz, CDCl$_3$) δ 5.31 (bs, 1H), 7.11 (d, 1H, J 7.26 Hz), 7.36-7.45 (m, 3H) 7.61 (d, 1H, J=7.25 Hz), 7.83 (d, 2H, J=8.28 Hz), 8.21-8.33 (m, 4H); MS (ESI): m/z 375 [M+H]$^+$.

Example 10

(5-(4-Chlorophenyl)-3-(4-(5-fluoro-1H-benzo[d]imidazol-2-yl)phenyl)-1,2,4-oxadiazole) 2c To a solution of 4-chloro benzoic acid (11c, 78 mg, 0.5 mmol) in dry DMF (3 mL) was added carbonyl diimidazole (97 mg, 0.6 mmol) under nitrogen atmosphere and the reaction mixture was stirred at 37° C. for 1 h. Then 9(Z)-4-(5-Fluoro-1H-benzo[d]imidazol-2-yl)-N'-hydroxybenzimidamide) (10b, 162 mg, 0.6 mmol) was added and reaction mixture was heated at 110° C. for about 18 h (monitored by TLC). The contents of the reaction were cooled to 25° C. and poured into ice-cold water (25 L), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 2c as off white solid 142 mg, in 60.8% yield. $^1$H NMR (300 MHz, CDCl$_3$) δ 5.31 (bs, 1H), 7.07 (d, 1H, J=7.3 Hz), 7.41-7.57 (m, 5H) 7.59 (d, 1H, J=7.3 Hz), 8.21-8.33 (m, 4H); MS (ESI): m/z 391 [M+H]$^+$.

Example 11

(3-(4-(5-Fluoro-1H-benzo[d]imidazol-2-yl)phenyl)-5-(4-methoxyphenyl)-1,2,4-oxadiazole) 2f To a solution of 4-methoxy benzoic acid (11f, 76 mg, 0.5 mmol) in dry DMF (3 mL) was added carbonyl diimidazole (97 mg, 0.6 mmol) under nitrogen atmosphere and the reaction mixture was stirred at 37° C. for 1 h. Then 9(Z)-4-(5-Fluoro-1H-benzo[d]imidazol-2-yl)-N'-hydroxybenzimidamide) (10b, 162 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 2f as off white solid 147 mg, in 63.7% yield. $^1$H NMR (500 MHz, CDCl$_3$) δ 3.89 (s, 3H), 7.08-7.21 (m, 3H), 7.58 (d, 1H, J=7.24 Hz), 7.68 (s, 1H), 7.91 (d, 2H, J=8.28 Hz), 8.27-8.32 (m, 4H); MS (ESI): m/z 387 [M+H]$^+$.

Example 12

(3-(4-(5-Fluoro-1H-benzo[d]imidazol-2-yl)phenyl)-5-(3,4,5-trimethoxyphenyl)-1,2,4-oxadiazole) 2i To a solution of 3,4,5-methoxy benzoic acid (11i, 106 mg, 0.5 mmol) in dry DMF (3 mL) was added carbonyl diimidazole (97 mg, 0.6 mmol) under nitrogen atmosphere and the reaction mixture was stirred at 37° C. for 1 h. Then 9(Z)-4-(5-Fluoro-1H-benzo[d]imidazol-2-yl)-N'-hydroxybenzimidamide) (10b, 162 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 2i as off white solid 160 mg, in 60% yield. $^1$H NMR (300 MHz, CDCl$_3$) δ 3.81 (s, 3H), 3.87 (s, 6H), 6.98-7.21 (m, 3H), 7.46 (s, 1H), 7.55 (d, 1H, J=7.28 Hz), 8.19-8.30 (dd, 4H, J=8.30, 7.93 Hz); MS (ESI): m/z 447 [M+H]$^+$.

Example 13

3-(4-(5-Chloro-1H-benzo[d]imidazol-2-yl)phenyl)-5-phenyl-1,2,4-oxadiazole (3a)

To a solution of benzoic acid (11a, 61 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(5-Chloro-1H-benzo[d]imidazol-2-yl)-N-hydroxybenzimidamide) (10c, 172 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 3a as off white solid 134 mg, in 60.1% yield. $^1$H NMR (500 MHz, CDCl$_3$) δ 5.28 (bs, 1H), 7.10 (t, 1H, J=7.27 Hz), 7.16-7.25 (m, 3H), 7.76 (d, 2H, J=8.27 Hz), 7.96 (d, 2H, J=8.28 Hz), 8.24 (dd, 4H, J=8.32, 5.65 Hz), MS (ESI): m/z 373 [M+H]+.

Example 14

(3-(4-(5-Chloro-1H-benzo[d]imidazol-2-yl)phenyl)-5-(4-fluorophenyl)-1,2,4-oxadiazole) 3b To a solution of 4-flouro benzoic acid (11b, 70 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(5-Chloro-1H-benzo[d]imidazol-2-yl)-N-hydroxybenzimidamide) (10c, 172 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 3b as off white solid 127 mg, in 54.4% yield. $^1$H NMR (300 MHz, CDCl$_3$) δ 7.21-7.35 (m, 3H), 7.57 (d, 1H, J=7.23 Hz), 7.75 (s, 1H), 7.87 (d, 2H, J=8.30 Hz), 8.26-8.30 (m, 4H); MS (ESI): m/z 391 [M+H]+.

Example 15

(3-(4-(5-Chloro-1H-benzo[d]imidazol-2-yl)phenyl)-5-(4-chlorophenyl)-1,2,4-oxadiazole) 3c To a solution of 4-chloro benzoic acid (11c, 78 mg, 0.5 mmol) in dry DMF (3 L) was added carbonyl diimidazole (0.6 mmol) under nitrogen atmosphere and the reaction mixture was stirred at 37° C. for 1 h. Then ((Z)-4-(5-Chloro-1H-benzo[d]imidazol-2-yl)-N-hydroxybenzimidamide) (10c, 172 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 3c as off white solid 134 mg, in 55.1% yield. $^1$H NMR (300 MHz, CDCl$_3$) δ 7.22 (d, 1H, J=7.24 Hz), 7.41-7.54 (m, 3H), 7.83 (s, 1H), 7.91 (d, 2H, J=8.12 Hz), 8.18-8.29 (m, 4H); MS (ESI): m/z 407 [M+H]+.

Example 16

(3-(4-(5-Chloro-1H-benzo[d]imidazol-2-yl)phenyl)-5-(4-methoxyphenyl)-1,2,4-oxadiazole) 3f To a solution of 4-methoxy benzoic acid (11f, 76 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(5-Chloro-1H-benzo[d]imidazol-2-yl)-N'-hydroxybenzimidamide) (10c, 172 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 3f as off white solid 126 mg, in 52.3% yield. $^1$H NMR (300 MHz, CDCl$_3$) δ 3.87 (s, 3H), 7.12-7.24 (m, 3H), 7.54 (d, 1H, J=7.32 Hz), 7.77 (s, 1H), 7.93 (d, 2H, J=8.21 Hz), 8.27-8.32 (m, 4H); MS (ESI): m/z 403 [M+H]+.

Example 17

(3-(4-(5-Chloro-1H-benzo[d]imidazol-2-yl)phenyl)-5-(3,4,5-trimethoxyphenyl)-1,2,4-oxadiazole) 3i To a solution of 3,4,5-trimethoxy benzoic acid (11i, 106 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)-4-(5-Chloro-1H-benzo[d]imidazol-2-yl)-N'-hydroxybenzimidamide) (10c, 172 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 3i as off white solid 476 mg, in 65% yield. $^1$H NMR (300 MHz, CDCl$_3$) δ 3.89 (s, 3H), 3.93 (s, 6H), 7.16-7.25 (m, 3H), 7.57 (d, 1H, J=7.2 Hz), 7.81 (s, 1H), 8.20-8.29 (m, 4H); MS (ESI): m/z 463 [M+H]+.

Example 18

(3-(4-(5-Methoxy-1H-benzo[d]imidazol-2-yl)phenyl)-5-phenyl-1,2,4-oxadiazole) 5a

To a solution of benzoic acid (11a, 61 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)—N'-Hydroxy-4-(5-methoxy-1H-benzo[d]imidazol-2-yl)benzimidamide) (10e, 169 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 5a as off white solid 139 mg, in 63% yield. $^1$H NMR (300 MHz, CDCl$_3$) δ 3.88 (s, 3H), 7.12-7.23 (m, 2H), 7.32-7.51 (m, 4H), 7.79 (d, 1H, J=7.23 Hz), 8.23-8.30 (m, 4H); MS (ESI): m/z 369 [M+H]+.

Example 19

(5-(4-Fluorophenyl)-3-(4-(5-methoxy-1H-benzo[d]imidazol-2-yl)phenyl)-1,2,4-oxadiazole) 5b To a solution of 4-flouro benzoic acid (11b, 70 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)—N'-Hydroxy-4-(5-methoxy-1H-benzo[d]imidazol-2-yl)benzimidamide) (10e, 169 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 5b as off white solid 129 mg, in 55.7% yield. $^1$H NMR (300 MHz, CDCl$_3$) δ 3.85 (s, 3H), 7.04-7.21 (m, 2H), 7.57-7.62 (m, 3H), 7.71 (d, 1H, J=7.24 Hz), 8.19-8.28 (m, 4H); MS (ESI): m/z 387 [M+H]$^+$.

Example 20

(5-(4-Chlorophenyl)-3-(4-(5-methoxy-1H-benzo[d]imidazol-2-yl)phenyl)-1,2,4-oxadiazole) 5c To a solution of 4-chloro benzoic acid (11c, 78 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)—N'-Hydroxy-4-(5-methoxy-1H-benzo[d]imidazol-2-yl)benzimidamide) (10e, 169 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 5c as off white solid 119 mg, in 49% yield. $^1$H NMR (500 MHz, CDCl$_3$) δ 3.83 (s, 3H), 7.02 (d, 1H, J=7.21 Hz), 7.21 (s, 1H), 7.54 (d, 2H, J=8.11 Hz), 7.59 (d, 1H, J=7.24 Hz), 7.83 (d, 2H, J=8.12 Hz), 8.21-8.32 (dd, 4H, J=8.3, 5.62 Hz); MS (ESI): m/z 403 [M+H]$^+$.

Example 21

(3-(4-(5-Methoxy-1H-benzo[d]imidazol-2-yl)phenyl)-5-(4-methoxyphenyl)-1,2,4-oxadiazole) 5f To a solution of 4-methoxy benzoic acid (11f, 76 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)—N'-Hydroxy-4-(5-methoxy-1H-benzo[d]imidazol-2-yl)benzimidamide) (10e, 169 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 5f as off white solid 125 mg, in 52.4% yield. $^1$H NMR (300 MHz, CDCl$_3$) δ 3.87 (s, 3H), 3.89 (s, 3H), 6.91 (d, 1H, J=7.24 Hz), 7.15 (s, 1H), 7.46-7.52 (m, 2H), 7.57 (d, 1H, J=7.26 Hz), 7.89-8.12 (m, 2H), 8.27-8.32 (m, 4H); MS (ESI): m/z 399 [M+H]$^+$.

Example 22

(3-(4-(5-Methoxy-1H-benzo[d]imidazol-2-yl)phenyl)-5-(3,4,5-trimethoxyphenyl)-1,2,4-oxadiazole) 5i To a solution of 3,4,5-trimethoxy benzoic acid (11i, 106 mg, 0.5 mmol) in dry DMF (3 mL) was added carbonyl diimidazole (97 mg, 0.6 mmol) under nitrogen atmosphere and the reaction mixture was stirred at 37° C. for 1 h. Then ((Z)—N'-Hydroxy-4-(5-methoxy-1H-benzo[d]imidazol-2-yl)benzimidamide) (10e, 169 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 5i as off white solid 157 mg, in 57.2% yield. $^1$H NMR (500 MHz, CDCl$_3$) δ 3.86 (s, 3H), 3.90 (s, 3H), 3.99 (s, 6H), 6.84 (d, 1H, J=8.68 Hz), 7.12 (s, 1H), 7.42 (s, 2H), 7.50 (d, 1H, J=8.68 Hz), 8.30 (dd, 4H, J=8.30, 7.93 Hz); MS (ESI): m/z 459 [M+H]$^+$.

Example 23

3-(4-(5-methyl-1H-benzo[d]imidazol-2-yl)phenyl)-5-(3,4,5-trimethoxyphenyl)-1,2,4-oxadiazole 6i To a solution of 3,4,5-trimethoxy benzoic acid (11i, 106 mg, 0.5 mmol) in dry DMF (3 mL) was added carbonyl diimidazole (97 mg, 0.6 mmol) under nitrogen atmosphere and the reaction mixture was stirred at 37° C. for 1 h. Then (Z)—N'-hydroxy-4-(5-methyl-1H-benzo[d]imidazol-2-yl)benzimidamide (10f, 160 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 6i as off white solid 155 mg, in 58% yield. $^1$H NMR (300 MHz, CDCl$_3$+DMSO-d6) δ 2.39 (s, 3H), 3.89 (s, 3H), 3.98 (s, 6H), 6.71-6.80 (m, 1H), 6.91 (s, 2H), 7.43-7.52 (m, 2H), 7.89-8.16 (dd, 4H, J=8.32, 5.64 Hz); MS (ESI): m/z 443 [M+H]$^+$.

Example 24

5-(4-methoxyphenyl)-3-(4-(5-(trifluoromethyl)-1H-benzo[d]imidazol-2-yl)phenyl)-1,2,4-oxadiazole 7f To a solution of 4-methoxy benzoic acid (11f, 76 mg, 0.5 mmol) in dry DMF (3 mL) was added carbonyl diimidazole (97 mg, 0.6 mmol) under nitrogen atmosphere and the reaction mixture was stirred at 37° C. for 1 h. Then (Z)—N'-hydroxy-4-(5-(trifluoromethyl)-1H-benzo[d]imidazol-2-yl)benzimidamide (10 g, 190 mg, 0.6 mmol) was added and reaction mixture was heated at 110° C. for about 18 h (monitored by TLC). The contents of the reaction were cooled to 25° C. and poured into ice-cold water (25 mL), extracted by ethyl acetate (3×15.0) and the combined organic phase was washed with brine, dried over anhydrous sodium sulfate, filtered and concentrated in vacuo. The obtained residue was purified by column chromatography using ethyl acetate-hexane as eluent to furnish 7f as off white solid 163 mg, in 63% yield. $^1$H NMR (300 MHz, DMSO-d6) δδ 3.87 (s, 3H), 6.88 (d, 2H, J=8.54 Hz), 7.62 (d, 2H, J=8.54 Hz), 7.78-7.91 (m, 2H), 7.31 (d, 1H, J=7.36 Hz), 8.11-8.27 (m, 4H); MS (ESI): m/z 437 [M+H]$^+$.

Biological Activity (Anticancer Activity)

The in vitro anticancer activity studies for these 3-(4-(1H-Benzo[d]imidazol-2-yl) phenyl)-5-phenyl-1,2,4-oxadiazole analogues were carried out at the National Cancer Institute, USA.

The 3-(4-(1H-Benzo[d]imidazol-2-yl) phenyl)-5-phenyl-1,2,4-oxadiazole analogues have been tested at NCI, USA, against sixty human tumor cell lines derived from nine cancer types (leukemia, non-small cell lung cancer, colon cancer, CNS cancer, melanoma cancer, ovarian cancer, renal cancer, prostate cancer and breast cancer). For these compounds results are expressed as growth inhibition ($GI_{50}$) values as per NCI protocol. The anticancer activity data of compounds 2i and 5i are shown in Table 1.

TABLE 1

In vitro cytotoxicity of compounds 2i and 5i in sixty human cancer cell lines

| Cancer panel/ Cell lines | $GI_{50}[\mu M]^a$ 2i | 5i |
|---|---|---|
| Leukemia | | |
| CCRF-CEM | 2.97 | 2.20 |
| HL-60 (TB) | 2.24 | 2.02 |
| K-562 | NT | 1.20 |
| MOLT-4 | 1.99 | 5.29 |
| RPMI-8226 | 1.94 | 6.02 |
| SR | 2.98 | 0.71 |
| Non-Small Cell Lung Cancer | | |
| A549/ATCC | 3.42 | 5.65 |
| EKVX | 3.45 | 26.2 |
| HOP-62 | 3.21 | 4.44 |
| HOP-92 | 1.76 | 14.3 |
| NCI-H226 | 2.72 | 2.27 |
| NCI-H23 | 2.50 | 4.10 |
| NCI-H322M | 1.30 | NT |
| NCI-H460 | 2.97 | 4.60 |
| NCI-H522 | 3.04 | 6.89 |
| Colon Cancer | | |
| COLO 205 | 4.77 | NT |
| HCC-2998 | 6.13 | 35.5 |
| HCT-116 | 2.13 | 1.90 |
| HCT-15 | 3.15 | 1.49 |
| HT29 | 3.69 | 2.70 |
| KM12 | 3.08 | 7.52 |
| SW-620 | 3.61 | 5.89 |
| CNS Cancer | | |
| SF-268 | 3.99 | 7.13 |
| SF-295 | 2.31 | 15.0 |
| SF-539 | 3.37 | 2.00 |
| SNB-19 | 5.62 | 1.27 |
| SNB-75 | 7.74 | 12.5 |
| U251 | 3.03 | 1.68 |
| Melanoma | | |
| LOX IMVI | 1.65 | 13.3 |
| MALME-3M | 2.32 | 1.67 |
| M14 | 3.23 | 5.47 |
| MDA-MB-435 | 2.73 | 4.27 |
| SK-MEL-2 | 4.21 | 18.9 |
| SK-MEL-28 | 3.78 | 9.59 |
| SK-MEL-5 | 2.22 | 3.25 |
| UACC-257 | 3.70 | 17.1 |
| UACC-62 | 2.35 | 14.0 |
| Ovarian Cancer | | |
| IGROV 1 | 3.81 | 26.3 |
| OVCAR-3 | 2.56 | 42.5 |
| OVCAR-4 | 2.82 | 1.88 |
| OVCAR-5 | 5.59 | 16.7 |

TABLE 1-continued

In vitro cytotoxicity of compounds 2i and 5i in sixty human cancer cell lines

| Cancer panel/ Cell lines | $GI_{50}[\mu M]^a$ 2i | 5i |
|---|---|---|
| OVCAR-8 | 2.36 | 4.93 |
| NCI/ADR-RES | 2.49 | 3.32 |
| SK-OV-3 | 4.12 | 25.3 |
| 786-0 | 3.61 | NT |
| A498 | 4.19 | 28.5 |
| ACHN | 3.72 | 28.2 |
| CAKI-1 | 2.76 | 23.4 |
| RXF 393 | 1.90 | 5.24 |
| SN 12C | 3.59 | 13.2 |
| TK-10 | 8.27 | 4.62 |
| UO-31 | 2.51 | 1.89 |
| Prostate Cancer | | |
| PC-3 | 2.33 | 240.5 |
| DU-145 | 3.96 | 9.48 |
| Breast Cancer | | |
| MCF-7 | 2.88 | 1.08 |
| MDA-MB-231/ATCC | 2.39 | 2.65 |
| HS 578T | 2.27 | 9.49 |
| BT-549 | 3.49 | 0.52 |
| T-47D | 2.72 | 14.7 |
| MDA-MB-468 | 3.01 | 6.54 |

$^a$Compound concentration required to decrease cell growth to half that of untreated cells. 2i (NSC: 761109/1), 5i (NSC: 761814/1).

The mean graph midpoint values of $Log_{10}\ GI_{50}$ as well as $Log_{10}\ LC_{50}$ for the compounds 2i, 5i and Hoechst 33258 (NSC-322921) is listed in Table 2. As demonstrated by mean graph pattern, compounds 2i and 5i exhibited an interesting profile of activity and selectivity for various cell lines.

TABLE 2

$Log_{10}\ GI_{50}$ and $Log_{10}\ LC_{50}$ mean graphs midpoints(MG_MID) of in vitro cytotoxicity data for the compounds 2i, 5i and Hoechst 33258 against nine cancer types.

| cancer type | $Log_{10}\ GI_{50}$ | | | $Log_{10}\ LC_{50}$ | | |
|---|---|---|---|---|---|---|
| | 2i | 5i | Hoechst 33258 | 2i | 5i | Hoechst 33258 |
| Leukemia | −5.64 | −5.48 | −4.73 | −4 | −4 | −2.81 |
| Non-small-celllung | −5.47 | −5.06 | −3.94 | −4.12 | −4.1 | −2.86 |
| Colon | −5.44 | −5.32 | −4.1 | −4.12 | −4.07 | −2.88 |
| CNS | −5.39 | −5.20 | −3.88 | −4.04 | −4.35 | −2.88 |
| Melanoma | −5.55 | −5.12 | −4.6 | −4.45 | −4.08 | −2.99 |
| Ovarian | −5.49 | −5.12 | −3.71 | −4.06 | −4.17 | −2.92 |
| Renal | −5.45 | −4.84 | −3.78 | −4.1 | −4.13 | −2.90 |
| Prostate | −5.51 | −4.85 | −3.2 | −4 | −4.04 | −2.85 |
| Breast | −5.55 | −5.47 | −4.67 | −4.03 | −4.1 | −2.84 |

Each cancer type represents the average of six to eight different cancer cell lines.

Classic antimitotic agents, such as taxanes and vinca alkaloids are widely used to treat human cancers. However, they have certain limitations in their clinical utility due to toxicity, p-glycoprotein-mediated drug resistance, difficult synthesis and isolation procedure. In this present invention, the synthesized compounds have shown significant anticancer activity with less toxicity to normal cells. One of the compound 5i has shown potent cytotoxicity on SR (leukemia cell line) and BT-549 (breast cancer cell line) with $GI_{50}$ values of 0.71 and 0.52 μM respectively.

The invention claimed is:
1. A compound of general formula A

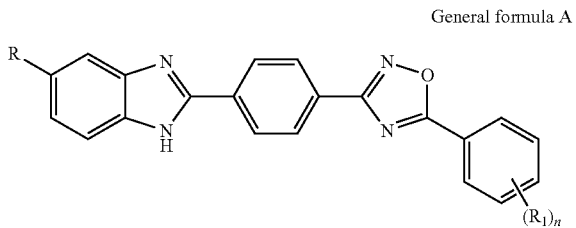

General formula A wherein
R is selected from the group consisting of H, F, Cl, Br, OMe, Me and CF$_3$,
R$_1$ is selected from the group consisting of H, 4-F, 4-Cl, 4-Br, 4-CF$_3$, 4-OMe, 3,4-OMe, 3,5-OMe and 3,4,5-OMe, and
n is an integer ranging from 1-3.

2. The compound as claimed in claim 1 selected from the group consisting of:
3-(4-(1H-Benzo[d]imidazol-2-yl)phenyl)-5-phenyl-1,2,4-oxadiazole (1a);
3-(4-(1H-Benzo[d]imidazol-2-yl)phenyl)-5-(4-fluorophenyl)-1,2,4-oxadiazole (1b);
3-(4-(1H-Benzo[d]imidazol-2-yl)phenyl)-5-(4-chlorophenyl)-1,2,4-oxadiazole (1c);
3-(4-(1H-Benzo[d]imidazol-2-yl)phenyl)-5-(4-bromophenyl)-1,2,4-oxadiazole (1d);
3-(4-(1H-Benzo[d]imidazol-2-yl)phenyl)-5-(4-(trifluoromethyl)phenyl)-1,2,4-oxadiazole (1e);
3-(4-(1H-Benzo[d]imidazol-2-yl)phenyl)-5-(4-methoxyphenyl)-1,2,4-oxadiazole (1f);
3-(4-(1H-Benzo[d]imidazol-2-yl)phenyl)-5-(3,4-dimethoxyphenyl)-1,2,4-oxadiazole (1g);
3-(4-(1H-Benzo[d]imidazol-2-yl)phenyl)-5-(3,5-dimethoxyphenyl)-1,2,4-oxadiazole (1h);
3-(4-(1H-Benzo[d]imidazol-2-yl)phenyl)-5-(3,4,5-trimethoxyphenyl)-1,2,4-oxadiazole (1i);
3-(4-(5-Fluoro-1H-benzo[d]imidazol-2-yl)phenyl)-5-phenyl-1,2,4-oxadiazole (2a);
3-(4-(5-Fluoro-1H-benzo[d]imidazol-2-yl)phenyl)-5-(4-fluorophenyl)-1,2,4-oxadiazole (2b);
5-(4-Chlorophenyl)-3-(4-(5-fluoro-1H-benzo[d]imidazol-2-yl)phenyl)-1,2,4-oxadiazole (2c);
5-(4-Bromophenyl)-3-(4-(5-fluoro-1H-benzo[d]imidazol-2-yl)phenyl)-1,2,4-oxadiazole (2d);
3-(4-(5-Fluoro-1H-benzo[d]imidazol-2-yl)phenyl)-5-(4-(trifluoromethyl)phenyl)-1,2,4-oxadiazole (2e);
3-(4-(5-Fluoro-1H-benzo[d]imidazol-2-yl)phenyl)-5-(4-methoxyphenyl)-1,2,4-oxadiazole (2f);
5-(3,4-Dimethoxyphenyl)-3-(4-(5-fluoro-1H-benzo[d]imidazol-2-yl)phenyl)-1,2,4-oxadiazole (2g);
5-(3,5-Dimethoxyphenyl)-3-(4-(5-fluoro-1H-benzo[d]imidazol-2-yl)phenyl)-1,2,4-oxadiazole (2h);
3-(4-(5-Fluoro-1H-benzo[d]imidazol-2-yl)phenyl)-5-(3,4,5-trimethoxyphenyl)-1,2,4-oxadiazole (2i);
3-(4-(5-Chloro-1H-benzo[d]imidazol-2-yl)phenyl)-5-phenyl-1,2,4-oxadiazole (3a);
3-(4-(5-Chloro-1H-benzo[d]imidazol-2-yl)phenyl)-5-(4-fluorophenyl)-1,2,4-oxadiazole (3b);
3-(4-(5-Chloro-1H-benzo[d]imidazol-2-yl)phenyl)-5-(4-chlorophenyl)-1,2,4-oxadiazole (3c);
3-(4-(5-Chloro-1H-benzo[d]imidazol-2-yl)phenyl)-5-(4-bromophenyl)-1,2,4-oxadiazole (3d);
3-(4-(5-Chloro-1H-benzo[d]imidazol-2-yl)phenyl)-5-(4-(trifluoromethyl)phenyl)-1,2,4-oxadiazole (3e);
3-(4-(5-Chloro-1H-benzo[d]imidazol-2-yl)phenyl)-5-(4-methoxyphenyl)-1,2,4-oxadiazole (3f);
3-(4-(5-Chloro-1H-benzo[d]imidazol-2-yl)phenyl)-5-(3,4-dimethoxyphenyl)-1,2,4-oxadiazole (3g);
3-(4-(5-Chloro-1H-benzo[d]imidazol-2-yl)phenyl)-5-(3,5-dimethoxyphenyl)-1,2,4-oxadiazole (3h);
3-(4-(5-Chloro-1H-benzo[d]imidazol-2-yl)phenyl)-5-(3,4,5-trimethoxyphenyl)-1,2,4-oxadiazole (3i);
3-(4-(5-Bromo-1H-benzo[d]imidazol-2-yl)phenyl)-5-phenyl-1,2,4-oxadiazole (4a);
3-(4-(5-Bromo-1H-benzo[d]imidazol-2-yl)phenyl)-5-(4-fluorophenyl)-1,2,4-oxadiazole (4b);
3-(4-(5-Bromo-1H-benzo[d]imidazol-2-yl)phenyl)-5-(4-chlorophenyl)-1,2,4-oxadiazole (4c);
3-(4-(5-Bromo-1H-benzo[d]imidazol-2-yl)phenyl)-5-(4-bromophenyl)-1,2,4-oxadiazole (4d);
3-(4-(5-Bromo-1H-benzo[d]imidazol-2-yl)phenyl)-5-(4-(trifluoromethyl)phenyl)-1,2,4-oxadiazole (4e);
3-(4-(5-Bromo-1H-benzo[d]imidazol-2-yl)phenyl)-5-(4-methoxyphenyl)-1,2,4-oxadiazole (4f);
3-(4-(5-Bromo-1H-benzo[d]imidazol-2-yl)phenyl)-5-(3,4-dimethoxyphenyl)-1,2,4-oxadiazole (4g);
3-(4-(5-Bromo-1H-benzo[d]imidazol-2-yl)phenyl)-5-(3,5-dimethoxyphenyl)-1,2,4-oxadiazole (4h);
3-(4-(5-Bromo-1H-benzo[d]imidazol-2-yl)phenyl)-5-(3,4,5-trimethoxyphenyl)-1,2,4-oxadiazole (4i);
3-(4-(5-Methoxy-1H-benzo[d]imidazol-2-yl)phenyl)-5-phenyl-1,2,4-oxadiazole (5a);
5-(4-Fluorophenyl)-3-(4-(5-methoxy-1H-benzo[d]imidazol-2-yl)phenyl)-1,2,4-oxadiazole (5b);
5-(4-Chlorophenyl)-3-(4-(5-methoxy-1H-benzo[d]imidazol-2-yl)phenyl)-1,2,4-oxadiazole (5c);
5-(4-Bromophenyl)-3-(4-(5-methoxy-1H-benzo[d]imidazol-2-yl)phenyl)-1,2,4-oxadiazole (5d);
3-(4-(5-Methoxy-1H-benzo[d]imidazol-2-yl)phenyl)-5-(4-(trifluoromethyl)phenyl)-1,2,4-oxadiazole (5e);
3-(4-(5-Methoxy-1H-benzo[d]imidazol-2-yl)phenyl)-5-(4-methoxyphenyl)-1,2,4-oxadiazole (5f);
5-(3,4-Dimethoxyphenyl)-3-(4-(5-methoxy-1H-benzo[d]imidazol-2-yl)phenyl)-1,2,4-oxadiazole (5g);
5-(3,5-Dimethoxyphenyl)-3-(4-(5-methoxy-1H-benzo[d]imidazol-2-yl)phenyl)-1,2,4-oxadiazole (5h);
3-(4-(5-Methoxy-1H-benzo[d]imidazol-2-yl)phenyl)-5-(3,4,5-trimethoxyphenyl)-1,2,4-oxadiazole (5i);
3-(4-(5-Methyl-1H-benzo[d]imidazol-2-yl)phenyl)-5-phenyl-1,2,4-oxadiazole (6a);
5-(4-Fluorophenyl)-3-(4-(5-methyl-1H-benzo[d]imidazol-2-yl)phenyl)-1,2,4-oxadiazole (6b);
5-(4-Chlorophenyl)-3-(4-(5-methyl-1H-benzo[d]imidazol-2-yl)phenyl)-1,2,4-oxadiazole (6c);
5-(4-Bromophenyl)-3-(4-(5-methyl-1H-benzo[d]imidazol-2-yl)phenyl)-1,2,4-oxadiazole (6d);
3-(4-(5-Methyl-1H-benzo[d]imidazol-2-yl)phenyl)-5-(4-(trifluoromethyl)phenyl)-1,2,4-oxadiazole (6e);
5-(4-Methoxyphenyl)-3-(4-(5-methyl-1H-benzo[d]imidazol-2-yl)phenyl)-1,2,4-oxadiazole (6f);
5-(3,4-Dimethoxyphenyl)-3-(4-(5-methyl-1H-benzo[d]imidazol-2-yl)phenyl)-1,2,4-oxadiazole (6g);
5-(3,5-Dimethoxyphenyl)-3-(4-(5-methyl-1H-benzo[d]imidazol-2-yl)phenyl)-1,2,4-oxadiazole (6h);
3-(4-(5-Methyl-1H-benzo[d]imidazol-2-yl)phenyl)-5-(3,4,5-trimethoxyphenyl)-1,2,4-oxadiazole (6i);
5-Phenyl-3-(4-(5-(trifluoromethyl)-1H-benzo[d]imidazol-2-yl)phenyl)-1,2,4-oxadiazole (7a);
5-(4-Fluorophenyl)-3-(4-(5-(trifluoromethyl)-1H-benzo[d]imidazol-2-yl)phenyl)-1,2,4-oxadiazole (7b);
5-(4-Chlorophenyl)-3-(4-(5-(trifluoromethyl)-1H-benzo[d]imidazol-2-yl)phenyl)-1,2,4-oxadiazole (7c);
5-(4-Bromophenyl)-3-(4-(5-(trifluoromethyl)-1H-benzo[d]imidazol-2-yl)phenyl)-1,2,4-oxadiazole (7d);

3-(4-(5-(Trifluoromethyl)-1H-benzo[d]imidazol-2-yl)
  phenyl)-5-(4-(trifluoromethyl)phenyl)-1,2,4-oxadiaz-
  ole (7e);
5-(4-Methoxyphenyl)-3-(4-(5-(trifluoromethyl)-1H-
  benzo[d]imidazol-2-yl)phenyl)-1,2,4-oxadiazole (7f);
5-(3,4-Dimethoxyphenyl)-3-(4-(5-(trifluoromethyl)-1H-
  benzo[d]imidazol-2-yl)phenyl)-1,2,4-oxadiazole (7g);
5-(3,5-Dimethoxyphenyl)-3-(4-(5-(trifluoromethyl)-1H-
  benzo[d]imidazol-2-yl)phenyl)-1,2,4-oxadiazole (7h);
  and
3-(4-(5-(Trifluoromethyl)-1H-benzo[d]imidazol-2-yl)
  phenyl)-5-(3,4,5-trimethoxyphenyl)-1,2,4-oxadiazole
  (7i).

3. The compound as claimed in claim 1, for use in the treatment of cancer selected from the group consisting of leukemia, melanoma, ovarian, colon, prostate and breast cancer.

4. The compound as claimed in claim 2, wherein compounds 5i and 2i exhibit cytotoxic activity against SR (leukemia cell line) and BT-549 (breast cancer cell line) for $GI_{50}$ values of 0.71 and 0.52 μM respectively.

5. A process for the preparation of compound of general formula A as claimed in claim 1, said process comprising the steps of:
  i. reacting a compound of formula 11 (a-i)

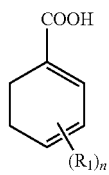

11 (a-i)

wherein $R_1$ is selected from the group consisting of H, 4-F, 4-Cl, 4-Br, 4-$CF_3$, 4-OMe, 3,4-OMe, 3,5-OMe and 3,4,5-OMe, and n is an integer ranging from 1-3;
with carbonyldiimidazole in a ratio ranging between 1:1 to 1:3, in dry DMF under nitrogen atmosphere followed by stirring at a temperature in the range of 35-37° C. for a period in the range of 50 to 60 minutes to obtain a first mixture;
  ii. adding amidoximes of formula 10(a-g) to the first mixture obtained in step (i) in the ratio ranging between 1:1 to 1:1.5, followed by heating at a temperature in the range of 110-115° C. for a period in the range of 16-18 hours to obtain a second mixture;

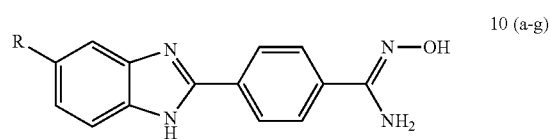

10 (a-g)

wherein R is selected from the group consisting of H, F, Cl, Br, Ome, Me and $CF_3$,
  iii. cooling the second mixture obtained in step (ii) at a temperature in the range of 20 to 25° C., pouring into ice-cold water, extracting, washing, drying, filtering and concentrating in vacuum followed by purifying by column chromatography to obtain the compound of general formula A.

6. A pharmaceutical composition comprising therapeutically effective amount of compound of general formula A as claimed in claim 1, optionally along with one or more pharmaceutically acceptable carriers, additives, lubricants and diluents.

\* \* \* \* \*